(12) United States Patent
Ssenyange et al.

(10) Patent No.: US 10,307,080 B2
(45) Date of Patent: Jun. 4, 2019

(54) RESPIRATORY MONITOR

(71) Applicant: Spirometrix, Inc., Pleasanton, CA (US)

(72) Inventors: Solomon Ssenyange, Fremont, CA (US); Ryan R. Leard, Oakland, CA (US); Patrick L. Rhodes, Pleasanton, CA (US); Jemal D. Zikria, Danville, CA (US)

(73) Assignee: Spirosure, Inc., Pleasanton, CA (US)

( * ) Notice: Subject to any disclaimer, the term of this patent is extended or adjusted under 35 U.S.C. 154(b) by 404 days.

(21) Appl. No.: 14/495,853

(22) Filed: Sep. 24, 2014

(65) Prior Publication Data

US 2015/0250408 A1 Sep. 10, 2015

Related U.S. Application Data

(60) Provisional application No. 61/949,871, filed on Mar. 7, 2014, provisional application No. 61/955,192, filed on Mar. 18, 2014.

(51) Int. Cl.
*A61B 5/08* (2006.01)
*A61B 5/097* (2006.01)
(Continued)

(52) U.S. Cl.
CPC ............ *A61B 5/097* (2013.01); *A61B 5/0022* (2013.01); *A61B 5/082* (2013.01); *A61B 5/083* (2013.01);
(Continued)

(58) Field of Classification Search
CPC ....... A61B 5/097; A61B 5/083; A61B 5/0022; A61B 5/082; G01N 2033/4975
See application file for complete search history.

(56) References Cited

U.S. PATENT DOCUMENTS

| | | |
|---|---|---|
| 4,812,648 A | 3/1989 | Perlman |
| 4,947,861 A | 8/1990 | Hamilton |
| (Continued) | | |

FOREIGN PATENT DOCUMENTS

| | | |
|---|---|---|
| CN | 102469954 A | 5/2012 |
| CN | 102596030 A | 7/2012 |
| (Continued) | | |

OTHER PUBLICATIONS

International Search Report and Written Opinion for International Application No. PCT/US 2015/019226, dated Aug. 14, 2015 (16 pages).

(Continued)

*Primary Examiner* — Jacqueline Cheng
*Assistant Examiner* — Tho Q Tran

(57) ABSTRACT

A respiratory monitor is disclosed that includes features for conducting multiple pulmonary function tests in a single device and for detecting the presence of nitric oxide in exhaled breath. Also described is a mouthpiece that allows for separate inhalation and exhalation pathways and for filtering inhaled and exhaled breath for predetermined species prior to exhalation into the respiratory monitor. The monitor further allows for wired, wireless and network connectivity and for cloud-based systems for communicating and correlating pulmonary data as well as relevant environmental data and displaying the data for use by patients and health care professionals.

2 Claims, 26 Drawing Sheets

(51) Int. Cl.
  *G01N 33/497* (2006.01)
  *G01N 33/00* (2006.01)
  *A61B 5/00* (2006.01)
  *A61B 5/083* (2006.01)

(52) U.S. Cl.
  CPC ....... *A61B 5/7246* (2013.01); *G01N 33/0013* (2013.01); *G01N 33/0016* (2013.01); *G01N 33/0037* (2013.01); *G01N 33/0073* (2013.01); *G01N 33/497* (2013.01); *A61B 2560/0242* (2013.01); *G01N 2033/4975* (2013.01)

(56) References Cited

U.S. PATENT DOCUMENTS

| | | | |
|---|---|---|---|
| 4,956,073 | A | 9/1990 | Pribat et al. |
| 5,081,871 | A | 1/1992 | Glaser |
| 5,447,165 | A | 9/1995 | Gustafsson |
| 5,531,218 | A | 7/1996 | Krebs |
| 5,565,075 | A | 10/1996 | Davis et al. |
| 5,795,787 | A | 8/1998 | Silkoff et al. |
| 5,922,610 | A * | 7/1999 | Alving ............... G01N 33/0037 422/83 |
| 59,222,610 | | 7/1999 | Alving et al. |
| 6,010,459 | A | 1/2000 | Silkoff et al. |
| 6,038,913 | A | 3/2000 | Gustafsson et al. |
| 6,099,480 | A | 8/2000 | Gustafsson |
| 6,468,222 | B1 | 10/2002 | Mault et al. |
| 6,475,158 | B1 | 11/2002 | Orr et al. |
| 6,612,306 | B1 | 9/2003 | Mault |
| 6,635,415 | B1 * | 10/2003 | Bollinger ............ G01N 21/766 422/81 |
| 6,723,056 | B1 | 4/2004 | Alving et al. |
| 6,733,463 | B2 | 5/2004 | Moilanen et al. |
| 6,764,591 | B1 | 7/2004 | Dutta et al. |
| 6,843,900 | B2 | 1/2005 | Dutta et al. |
| 6,866,637 | B2 | 3/2005 | George et al. |
| 7,014,692 | B2 | 3/2006 | Nilsson et al. |
| 7,045,359 | B2 | 5/2006 | Birks et al. |
| 7,108,659 | B2 | 9/2006 | Ross et al. |
| 7,270,638 | B2 | 9/2007 | Lundberg et al. |
| 7,352,465 | B2 | 4/2008 | Fay et al. |
| 7,427,269 | B2 | 9/2008 | George et al. |
| 7,611,613 | B2 | 11/2009 | Dutta et al. |
| 7,678,062 | B2 | 3/2010 | George et al. |
| 7,687,275 | B2 | 3/2010 | Burdinski |
| 7,694,547 | B2 | 4/2010 | Dutta et al. |
| 7,704,214 | B2 | 4/2010 | Abraham-Fuchs et al. |
| 7,814,777 | B2 | 10/2010 | Van Kesteren |
| 7,846,739 | B2 | 12/2010 | von Bahr et al. |
| 8,040,516 | B2 | 10/2011 | Van Kesteren et al. |
| 8,057,653 | B2 | 11/2011 | Dutta et al. |
| 8,109,128 | B2 | 2/2012 | Kalkman et al. |
| 8,144,675 | B1 | 3/2012 | Loc et al. |
| 8,176,915 | B2 | 5/2012 | Jaffe et al. |
| 8,322,190 | B2 | 12/2012 | Kalkman et al. |
| 8,425,428 | B2 | 4/2013 | Wood |
| 8,796,034 | B2 | 8/2014 | von Bahr et al. |
| 9,164,080 | B2 | 10/2015 | Dutta et al. |
| 2002/0185129 | A1 * | 12/2002 | Fisher ................ A61B 5/0836 128/203.25 |
| 2006/0027465 | A1 | 2/2006 | Nair et al. |
| 2006/0195040 | A1 | 8/2006 | Nason et al. |
| 2007/0281362 | A1 | 12/2007 | Vink et al. |
| 2008/0077037 | A1 | 3/2008 | Gouma et al. |
| 2008/0261332 | A1 | 10/2008 | Burdinski |
| 2009/0128819 | A1 | 5/2009 | Van Kesteren et al. |
| 2009/0229345 | A1 | 9/2009 | Van Kesteren |
| 2009/0248961 | A1 | 10/2009 | Van Dijk et al. |
| 2009/0288474 | A1 | 11/2009 | Kalkman et al. |
| 2010/0011836 | A1 | 1/2010 | Kalkman et al. |
| 2010/0020326 | A1 | 1/2010 | Van Kesteren |
| 2010/0043526 | A1 | 2/2010 | Helwegen et al. |
| 2010/0045990 | A1 | 2/2010 | Van Kesteren et al. |
| 2010/0081955 | A1 | 4/2010 | Wood, Jr. et al. |
| 2010/0089121 | A1 | 4/2010 | Hemmingsson et al. |
| 2010/0106039 | A1 | 4/2010 | Abraham-Fuchs et al. |
| 2010/0121212 | A1 | 5/2010 | Carlsson et al. |
| 2010/0137733 | A1 | 6/2010 | Wang et al. |
| 2010/0268106 | A1 | 10/2010 | Johnson et al. |
| 2011/0009762 | A1 | 1/2011 | Eichler et al. |
| 2011/0035158 | A1 | 2/2011 | Banos et al. |
| 2011/0046497 | A1 | 2/2011 | Abraham-Fuchs et al. |
| 2011/0066060 | A1 | 3/2011 | von Bahr et al. |
| 2011/0077545 | A1 * | 3/2011 | Eichler ................ A61B 5/097 600/538 |
| 2011/0158939 | A1 | 6/2011 | Tepper et al. |
| 2011/0239735 | A1 | 10/2011 | Setayesh et al. |
| 2011/0277536 | A1 | 11/2011 | McFaul |
| 2012/0006102 | A1 | 1/2012 | Bryant et al. |
| 2012/0065535 | A1 | 3/2012 | Abraham-Fuchs et al. |
| 2012/0113241 | A1 | 5/2012 | Shieh et al. |
| 2012/0123288 | A1 * | 5/2012 | Van Kesteren ........ A61B 5/082 600/532 |
| 2012/0203126 | A1 | 8/2012 | Kahlman et al. |
| 2012/0271188 | A1 | 10/2012 | Van Kesteren |
| 2012/0310104 | A1 | 12/2012 | Van Kesteren et al. |
| 2013/0219988 | A1 | 8/2013 | Dutta et al. |
| 2013/0219995 | A1 | 8/2013 | Dutta et al. |
| 2013/0327122 | A1 | 12/2013 | Dutta et al. |
| 2014/0278144 | A1 * | 9/2014 | Risk .................. G01N 21/3504 702/24 |
| 2017/0065208 | A1 | 3/2017 | Furusaki et al. |

FOREIGN PATENT DOCUMENTS

| | | |
|---|---|---|
| CN | 106163394 A | 11/2016 |
| EP | 0606351 B1 | 8/1999 |
| EP | 0724723 B1 | 4/2000 |
| EP | 1384069 B1 | 6/2006 |
| EP | 1439781 B1 | 6/2006 |
| EP | 1661514 B1 | 7/2008 |
| EP | 1836477 B1 | 6/2011 |
| EP | 2082214 B1 | 7/2011 |
| EP | 1883803 B1 | 6/2012 |
| EP | 3113683 | 1/2017 |
| JP | H01-132956 | 2/1989 |
| JP | 2005538819 A | 12/2005 |
| JP | 2006133039 A | 5/2006 |
| JP | 2009533682 A | 9/2009 |
| JP | 2017-515614 A | 6/2017 |
| RU | 2143689 C1 | 12/1999 |
| RU | 2016 136 114 A | 4/2018 |
| WO | WO 2004023997 A1 | 3/2004 |
| WO | WO 2005088289 A1 | 9/2005 |
| WO | WO 2006054114 A1 | 5/2006 |
| WO | WO 2006072867 A1 | 7/2006 |
| WO | WO 2006092751 | 9/2006 |
| WO | WO 2006114766 | 11/2006 |
| WO | WO 2007029164 | 3/2007 |
| WO | WO 2007120780 A2 | 10/2007 |
| WO | WO 2008026146 | 3/2008 |
| WO | WO 2008026183 | 3/2008 |
| WO | WO 2008026189 | 3/2008 |
| WO | WO 2008/052104 A2 | 5/2008 |
| WO | WO 2008052104 A2 | 5/2008 |
| WO | WO 2008056307 | 5/2008 |
| WO | WO 2008056312 | 5/2008 |
| WO | WO 2008144433 | 11/2008 |
| WO | WO 2009144628 | 12/2009 |
| WO | WO 2010070544 | 6/2010 |
| WO | WO 2011013046 | 2/2011 |
| WO | WO 2011055286 A1 | 2/2011 |
| WO | WO 2011048536 | 4/2011 |
| WO | WO 2011055286 A1 | 5/2011 |
| WO | WO 2011055286 | 5/2011 |
| WO | WO 2011101776 | 8/2011 |
| WO | WO 2012059835 | 5/2012 |
| WO | 2012135655 | 10/2012 |

(56) References Cited

FOREIGN PATENT DOCUMENTS

| WO | WO 2013003429 | 1/2013 |
|---|---|---|
| WO | WO 2015134895 A1 | 9/2015 |

OTHER PUBLICATIONS

Certificate of Correction for U.S. Pat. No. 6,866,637 (1 page).
Excerpts from file history for U.S. Appl. No. 11/903,135 (205 pages).
Excerpts from file history for U.S. Appl. No. 11/348,943 (231 pages).
Excerpts from file history for U.S. Appl. No. 12/242,887 (221 pages).
Excerpts from file history for U.S. Appl. No. 12/525,301 (256 pages).
Excerpts from file history for U.S. Appl. No. 12/594,573 (182 pages).
Excerpts from file history for U.S. Appl. No. 12/859,388 (265 pages).
Excerpts from File History for U.S. Appl. No. 12/947,096 (339 pages).
File History for European Patent Application No. EP08755591.8 (185 pages).
File History for European Patent No. 1075659 (219 pages).
File History for European Patent No. 1819274 (125 pages).
File History for Reexamination Request No. 90/008,309 (U.S. Pat. No. 6,010,459) (135 pages).
File History for U.S. Pat. No. 5,795,787 (357 pages).
File History for U.S. Pat. No. 5,922,610 (371 pages).
File History for U.S. Pat. No. 6,010,459 (450 pages).
File History for U.S. Pat. No. 6,038,913 (169 pages).
File History for U.S. Pat. No. 6,099,480 (127 pages).
File History for U.S. Pat. No. 6,723,056 (113 pages).
File History for U.S. Pat. No. 6,733,463 (107 pages).
File History for U.S. Pat. No. 7,014,692 (135 pages).
File History for U.S. Pat. No. 7,352,465 (197 pages).
File History for U.S. Pat. No. 7,846,739 (578 pages).
Logan Reserch Ltd., "LR2000 Series A New Generation of Mobile, Integrated, Clinical, Real-Time Nitric Oxide Gas Analysers," Instruction Manual (37 pages).
U.S. Appl. No. 60/090,445, entitled "A Robust High Temperature Semiconductiong CO Sensor," Date of Deposit Mar. 1, 2007 (17 pages).
U.S. Appl. No. 61/604,752, entitled "Obtaining Selectivity in Gas Sensors via a Sensor Array System Composed of P and N Type Material" (20 pages).
Patent Cooperation Treaty: Notification Concerning Transmittal of International Preliminary Report on Patentability (Chapter I of the Patent Cooperation Treaty) for International application No. PCT/2015/019226, dated Sep. 22, 2016 (12 pages).
Patent Cooperation Treaty: First Notice Informing the Applicant of the Communication of the International Application (To Designated Offices Which Do Not Apply the 30 Month Time Limit Under Article 22(1)) for International application No. PCT/2015/019226, dated Oct. 8, 2015 (1 Page).
Patent Cooperation Treaty: Notification of Transmittal of the International Search Report and the written Opinion of the International Searching Authority, or the Declaration for International application No. PCT/US2017/042459, dated Oct. 2, 2017 (14 Pages).
Pantalei Simone et al, "Improving sensing features of a nanocomposite PEDOT:PSS sensor for NO breath monitoring," Sensors and Actuator B: Chemical, Elsevier BV, vol. 179, Oct. 23, 2012, pp. 87-94.
European Patent Office, Communication pursuant to Article 94(3) EPC for Patent Application No. 15 713 594.8-1657, dated Oct. 27, 2017 (4 pages).
Reply to examination report to the European Patent Office for Patent Application No, 15713594.8, dated Mar. 6, 2018 (15 pages).
European Patent Office, Communication pursuant to Article 94(3) EPC for Patent Application No. 15 713 594.8-1115, dated Jul. 13, 2018 (4 pages).
Japan Patent Office, Office Action for Application No. 2016-573705, drafted Jul. 13, 2018 (4 pages).
Federal Service for Intellectual Property, Request of substantive examination for Application No. 2016136114/14 (056690), dated Nov.9.2018 (8 pages).
China National Intellectual Property Administration, First Office Action Issued by China National Intellectual Property Administration for PRC (China) Patent Application No. 201580012268.X, dated: Sep. 25, 2018 (10 pages).

\* cited by examiner

RESPIRATORY MONITOR

CROSS-REFERENCE TO RELATED APPLICATIONS

This application claims priority from and is related to the following prior applications: U.S. Provisional Application No. 61/949,871, filed Mar. 7, 2014, and U.S. Provisional Application No. 61/955,192, filed Mar. 18, 2014. These prior applications, including the entire written descriptions and drawing figures, are hereby incorporated into the present application by reference in their entirety.

FIELD OF THE INVENTION

The present invention relates generally to monitoring devices used to measure pulmonary functions, and more particularly to spirometry testing and testing for nitric oxide, as well as other markers, associated with monitoring respiratory medical conditions.

BACKGROUND

Respiratory diseases are some of the most common disorders in the world. Such respiratory diseases included conditions such as COPD, asthma, cystic fibrosis and pulmonary fibrosis. Chronic obstructive pulmonary disease (COPD), for example, affects millions of people and is responsible for extensive morbidity and mortality in the United States. COPD is a term used to describe chronic lung diseases characterized by progressive development of airflow limitation that is usually not fully reversible with medication. The common symptoms of COPD include breathlessness, wheezing and a chronic cough.

Asthma is another example of a chronic lung disease with symptoms similar to COPD, such as breathlessness and wheezing, but etiologically distinct from COPD. Asthma is a prevalent health care problem; it affects millions in the United States and around the world. About 40% of patients with asthma can be classified as having moderate to severe asthma and would benefit from more frequent monitoring of their airway inflammation. Although COPD and asthma require different treatments, test results for COPD and asthma often overlap.

Asthma in particular is characterized by an inflammatory reaction in hyper-reactive airways that restrict airflow into the lungs. In recent years, measurement of exhaled nitric oxide (eNO) has been shown to be a non-invasive and complementary tool to other pulmonary function tests in assessing airway inflammation, specifically in subjects with asthma. Accordingly, the presence of eNO has become a well-known, globally accepted biomarker for airway inflammation.

Nitric oxide is produced endogenously in cells by NO synthase and secreted by eosinophils in the distal alveoli. Its production is increased in response to inflammatory cytokines (which is associated with asthmatic episodes), and exhaled NO is thought to be an indirect measurement of airway eosinophilic inflammation. Thus, nitric oxide exhaled from the lower airways (e.g. non-nasal airways) can be correlated with the degree of airway inflammation. Patients with asthma have high levels of NO in their exhaled breath. Nitric oxide levels increase prior to the presence of clinical symptoms and its levels decline in response to appropriate therapy as airway inflammation subsides. These two characteristics make this an ideal biomarker for managing asthma status. For this reason, in 2011, the American Thoracic Society (ATS) issued new guidelines recommending the measurement of exhaled nitric oxide for the diagnosis and management of asthma. A diagnosis of asthma can be made when the level of nitric oxide in exhaled breath exceeds 50 ppb. High eNO levels are also associated with other inflammatory respiratory conditions.

In diagnosing respiratory diseases, a series of tests are routinely conducted. A common pulmonary function test (PFT) is spirometry, which measures obstruction of an individual's airway. A decreased maximum/forced lung exhalation rate often suggests airway obstruction. Results from the spirometry test can be used to estimate lung function and aid in assessing respiratory diseases and conditions. In the spirometry test, the patient expels air forcefully into a device to measure the amount (volume) of air or the air speed (flow) exhaled in one complete breath. The commonly used techniques to measure eNO require a subject to exhale into a device containing an NO sensor (online) or into a reservoir that can be analyzed later (offline). Since the concentration of eNO is inversely related to flow rate where lower exhalation rates allow more time for eNO to enter from the airway, the eNO test requires a user to exhale at a steady flow rate, normally at 50 ml/sec. As describe above, the level of eNO, measured in parts per billion (ppb), is significantly higher among asthmatic patients compared to healthy individuals.

Although the spirometry test is a common method of measuring airflow obstruction and can facilitate the monitoring of pulmonary disorders, the overlapping results in some conditions of COPD and asthma limit the use of the spirometry test alone for differentiating COPD from asthma. Additional investigations employing eNO tests, CT scans or pulse oximetry are also commonly employed to aid in assessing pulmonary diseases and conditions.

There are a number of challenges in current pulmonary function testing. Pulmonary function tests employ devices that are typically large and require the patient to be present in the physician's office or in the hospital for the tests. Moreover, the tests require separate devices, since in assessing respiratory disorders and conditions, separate measurement protocols are required for spirometry and for eNO testing. Typically, NO is measured in a clinical setting at a hospital or a physician's office for diagnostic purposes. The devices are expensive to purchase and maintain. Patients who have the most to gain from regular NO monitoring do not have regular access to accurate NO measuring equipment without frequent visits to their doctors. Thus, for at least the millions of people with moderate to severe asthma, there is a need for a cost-effective device that allows weekly or daily NO monitoring at home Another challenge in current standard pulmonary function testing is the accuracy and efficiency of the testing. An effective eNO test would be complimentary to the standard tests, but there is a dearth of inexpensive sensors capable of detecting the minute amounts of NO (typically measured in parts per billion) present in exhaled air. Moreover, NO sensors need to provide an accurate NO measurement in the presence of other possibly interfering gas components, including water and carbon dioxide ($CO_2$). A further challenge for NO measurement is the difficulty in distinguishing between nitric oxide (NO) and nitrogen dioxide ($NO_2$) in a patient's breath. That is, the gas introduced from the patient's breath typically has concentrations of NO, $NO_2$, carbon monoxide (CO), and oxygen ($O_2$). Traditional sensors are often unselective or incapable of distinguishing between the two main $NO_x$ components of interest, NO and $NO_2$, resulting in erroneous readings.

Thus, it would be desirable and advantageous to provide an accurate, efficient and portable respiratory monitor capable of conducting multiple pulmonary function tests, as well as other associated measurements, in a single device. It would also be desirable and advantageous to provide such a device that further allows for the remote monitoring of testing data, thereby avoiding the necessity for patients to make trips to doctor offices and hospitals. Additionally, it would be desirable and advantageous to provide such a respiratory monitor that allows for correlation of respiratory data to other relevant environmental data that can be presented in an efficient and easily understandable format.

SUMMARY

The present invention relates to respiratory monitors that incorporate nitric oxide detectors wherein exhaled breath from a user enters the detection device via a sample inlet that leads to a flow pathway within the detection device. In the flow pathway, one or more humidity equilibrators equilibrate the humidity of the breath sample in the flow pathway to the humidity of the ambient air to produce a humidity equilibrated breath sample. A catalytic filter in the flow pathway then receives the humidity equilibrated sample and generates a known equilibrium mixture of NO and $NO_2$ from $NO_x$. A $NO_x$ sensor positioned in the flow pathway then measures the $NO_x$ concentration in the sample. A controller thereafter calculates the total NO in the sample based on the measured $NO_x$ concentration and the known equilibrium.

In another aspect of the invention, one or more respiratory functions can be measured in a single device. The monitoring device comprises a housing that contains an inlet section positioned in the housing and configured to receive a gaseous sample, e.g., air expelled from a subject's lungs. A measuring section is located adjacent to the inlet section, along with a flow detection component positioned within the inlet section and configured to measure the flow rate of a gaseous sample entering the inlet section. An adjustable airflow restriction component is positioned upstream of the flow detection component. An adjustable partition can also be positioned downstream of the flow detection component for further directing and restricting air flow in the device. At least one gas detection sensor is positioned in the measuring section and configured to measure the presence of a predetermined gas contained in a gaseous sample received in the inlet section.

In another aspect of the invention, the gas detection sensor includes at least one electrochemical nitric oxide (NO) sensor configured to detect exhaled NO at aperture-directed flow rates.

The device can further include an optical sensor configured to perform blood flow measurements, and also include an accelerometer configured to perform respiratory measurements.

If desired, the device can further include an electronic controller integrated with the device and electronically coupled with the sensors. The controller can be configured to enter user information, execute programs, receive signals from the sensors and transmit data to a selected network or other remote locations.

In another aspect of the invention, a mouthpiece for users of monitoring devices permits fresh air to be inhaled through the mouthpiece via a dedicated pathway, and exhaled through the mouthpiece and into the monitoring device via a separate dedicated pathway. One or more filtering agents, filters or filtering media can be incorporated into one or both of the pathways to permit the screening of certain gaseous components, for example, $NO_x$.

In another aspect of the invention, spirometry and nitric oxide measurements can be correlated with selected environmental factors and presented in an easily understandable format. The devices described herein can be adapted to communicate measurements by wired or wireless technology and maintain data in the cloud for remote monitoring, access, and predictive analytics.

BRIEF DESCRIPTION OF THE DRAWINGS

Embodiments, which use the principles of the present invention, are illustrated with reference to the accompanying drawings.

DETAILED DESCRIPTION

Figure 1:
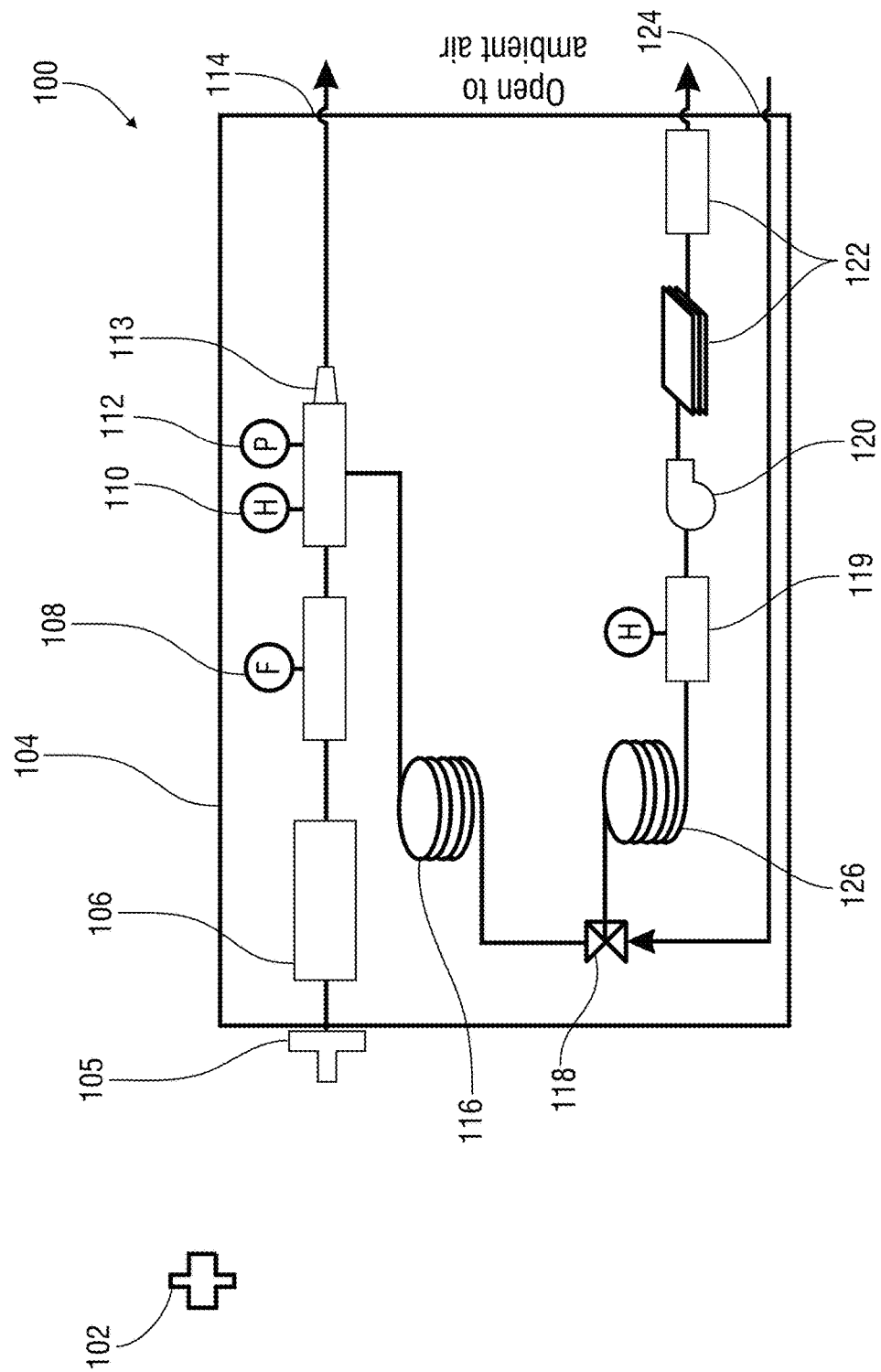
FIG. 1 is a schematic illustrating one embodiment of an NO detection device.

As used herein, the terms "comprises," "comprising," "includes," "including," "has," "having," or any other variation thereof, are intended to cover a non-exclusive inclusion. For example, processes, methods, articles, or apparatuses that comprise a list of elements are not necessarily limited to only those elements but may include other elements not expressly listed or inherent to such processes, methods, articles, or apparatuses. Further, unless expressly stated to the contrary, "or" refers to an inclusive "or" but not to an exclusive "or". For example, a condition A or B is satisfied by any one of the following: A is true (or present) and B is false (or not present), A is false (or not present) and B is true (or present), and both A and B are true (or present).

Also, use of "a" or "and" are employed to describe the elements and components of the invention. This is done merely for convenience and to give a general sense of the invention. This description includes one or at least one and the singular also includes the plural unless it is obvious that it is meant otherwise.

Unless otherwise defined, technical and scientific terms used herein have the same meaning as commonly understood by one of ordinary skill in the art to which this invention belongs. Although methods that are similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, materials, methods, and examples are illustrative only and not intended to be limiting.

In the following description, numerous specific details, such as the identification of various system components, are provided to understand the embodiments of the invention. One skilled in the art will recognize, however, that embodiments of the invention can be practiced without one or more of the specific details, ordinary methods, components, materials, etc. In still other instances, well-known structures, materials, or operations are not shown or described in detail to avoid obscuring aspects of various embodiments of the invention.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or work characteristics may be combined in any suitable manner in one or more embodiments.

In one aspect, the present respiratory monitor allows for the detection of nitric oxide in exhaled breath, taking into account variables such as humidity, temperature, pressure, and flow rate. In general, an exhaled breath sample is received in the monitor through a sample inlet. The sample proceeds along a flow pathway and is equilibrated for humidity. The humidity-equilibrated sample proceeds along the pathway to a catalytic filter adapted to generate a known equilibrium mixture of NO and $NO_2$ from $NO_x$. Thereafter, the sample flows to an NO sensor configured to measure the $NO_x$ concentration in the humidity-equilibrated sample. A controller thereafter calculates the total NO in the sample. A detailed description is set out below of various embodiments of the present monitor that further illustrate the present invention.

Referring to FIG. 1, an NO detection device 100 is shown with a disposable mouthpiece 102 connected to a detection box 104 directly or by way of flexible hose. The detection box 104 is illustrated showing (in direction of air flow): an inlet 105 for receiving a breath sample, a desiccant 106, such as activated alumina, a flow sensor 108, humidity sensor 110 and pressure sensor 112, and a flow restrictor 113. Following the flow restrictor 113, a first portion of the sample can exit the system at an outlet 114. In this embodiment, a second portion of the sample can branch off from the first portion, before flow restrictor 113, and continue through the detection box 104 for analysis. The second portion can thus pass through a humidity equilibrator 116, such as nafion tubing, a 3-way control valve 118, another humidity equilibrator 126, such has nafion tubing, a humidity sensor 119, a pump 120, and a microchannel reactor/sensor assembly 122. Further, ambient air is brought into the system through an inlet 124 (through the 3-way control valve 118). Ambient air then passes through the humidity equilibrator 126, humidity sensor 119, pump 120, and the microchannel reactor/sensor assembly 122.

The flow restrictor 113 can advantageously be used to further partition the sample (as the remainder is sent through the outlet 114). That is, the flow restrictor 113 can act to create back pressure at the inlet 105 and in the user's airways that closes the user's velum (soft palate), thereby preventing nasal breath from entering the mouth and subsequently being passed through the mouthpiece. Pulling the sample portion off of the main breath can advantageously maintain the volume and flow rate of gas analyzed at a constant level. Further, siphoning off a sample of breath can reduce the power consumption and size of the device 100, enabling the device to be battery operated. That is, the smaller gas volume can be filtered, heated, and analyzed using lower amounts of power and/or smaller components than a higher gas volume would take to analyze.

The humidity equilibrators 116, 126 can include a selectively permeable membrane, such as nafion tubes (polymer-based tubes), that selectively allow water molecules to pass through the wall of said tubing, thereby equilibrating the moisture content within the tube to the moisture content external to the tube while concurrently not affecting the concentration of NO, $NO_2$, or $NO_x$ within the tube as it passes along the length of the tube. The humidity equilibrators 116, 126 can thus be used to equilibrate humidity of the breath sample to ambient conditions. The humidity equilibrators can also be used in combination with the desiccant 106.

To enhance the accuracy of the NO detection by the microchannel reactor/sensor assembly 122, it is generally desirable to maintain a substantially constant humidity in the system. In the embodiment illustrated, ambient air is drawn into the system through the inlet 124. Further, the humidity equilibrators 116, 126 equilibrate the humidity of the breath sample to ensure that the breath sample has substantially the same humidity as the ambient air. The first humidity equilibrator 116 reduces the humidity of the sample breath only while the second humidity equilibrator 126 ensures that both the breath sample and the ambient air have a substantially equivalent controlled amount of humidity.

The microchannel reactor and sensor assembly 122 are configured to determine the total NO concentration from the breath sample gas. A patient's breath sample can include $NO_x$, which includes pure NO, pure $NO_2$, and mixtures thereof. The gas introduced from the patient's breath typically has concentrations of NO, $NO_2$ and carbon monoxide (CO) in the range of 0 to 1000 ppb. Further, the gas typically contains 14-18% oxygen ($O_2$). As illustrated, the microchannel reactor and sensor assembly 122 includes a catalyst filter comprising platinum and zeolite within the flow pathway.

The gas flowing through the flow pathway interacts with the catalyst filter at a particular temperature to form an equilibrium mixture of NO and $NO_2$. The microchannel reactor and sensor assembly 122 further includes a sensor element configured to sense the amount of $NO_x$ flowing therethrough. In the embodiment shown, the sensor element includes two electrodes on a solid electrolyte yttria-stabilized zirconia as follows: (1) a sensing potentiometric electrode disposed downstream of the catalytic filter device so as to contact the equilibrium mixture of NO and $NO_2$, and (2) a reference potentiometric electrode. Because the relative amounts of NO and $NO_2$ are known due to the equilibrium reaction through the filter, the $NO_x$ reading of the sensor can be used to determine the amount of NO in the sample.

Figure 8:
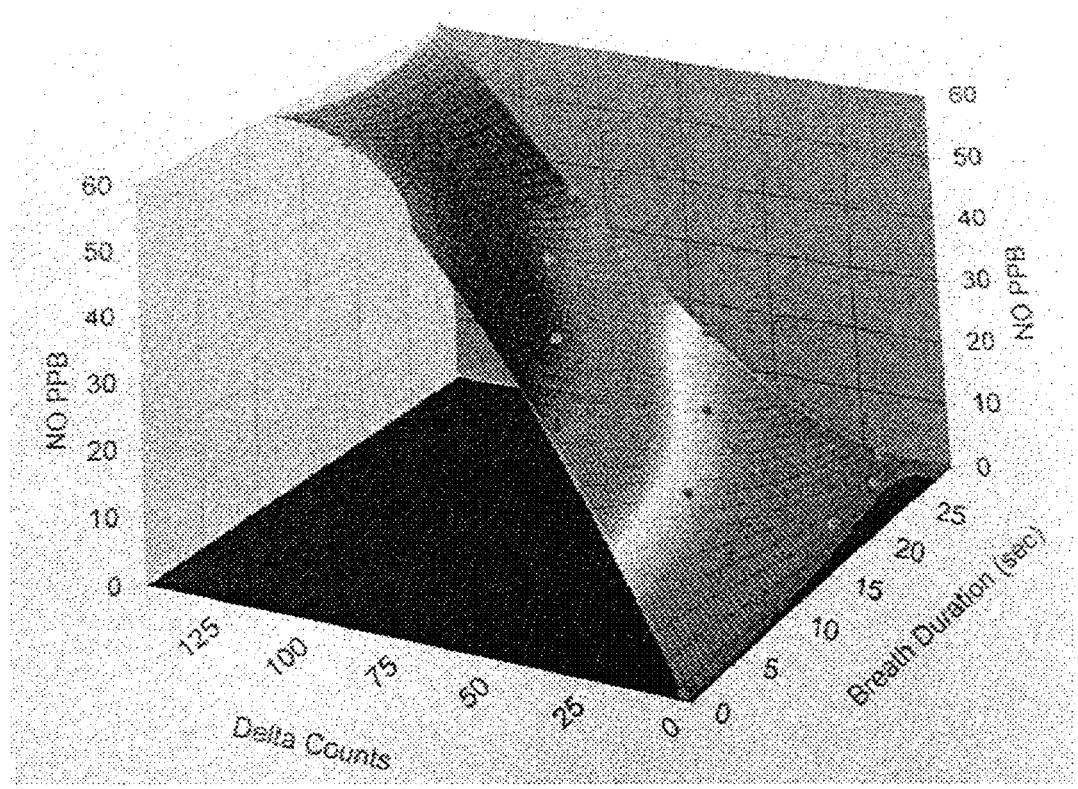
FIG. 8 is an example of a calibration curve.

The sensor and the microchannel reactor are maintained at different temperatures to provide a driving force for the $NO_x$ equilibration reactions. That is, the reactor equilibrates the NO to $NO_2$ mixture based principally on the temperature of the reactor (which includes platinum-zeolite (PtY)), and then the potential develops on the sensor element based on this equilibration of NO and $NO_2$ changing when reacting with reference electrode (PtY) and the sensing electrode at a temperature different than the temperature of the reactor. The sensor works by measuring the potential difference between the two electrodes, and a total $NO_x$ concentration (and then NO concentration) can be calculated by comparing the potential to a calibration curve. An example of such a calibration curve is illustrated in FIG. 8, which is generated by passing gas mixtures of known concentrations through the detection box 104. The sensor response may be dependent on the duration of the exposure to the sensing element, and thus the exposure duration is included in the example calibration curve of FIG. 8. The flow rate of the gas over the sensing element may also affect the sensor response, but flow rate is well controlled in this embodiment such that flow is not a factor for calibration.

Details regarding a reactor and sensor is described in U.S. Pat. No. 6,764,591, titled "Potentiometric sensors comprising yttria-stabilized zirconia and measurement method of total NOx sensing without CO interference," the entirety of which is incorporated by reference herein.

Figures 6A, 6B, 6C:
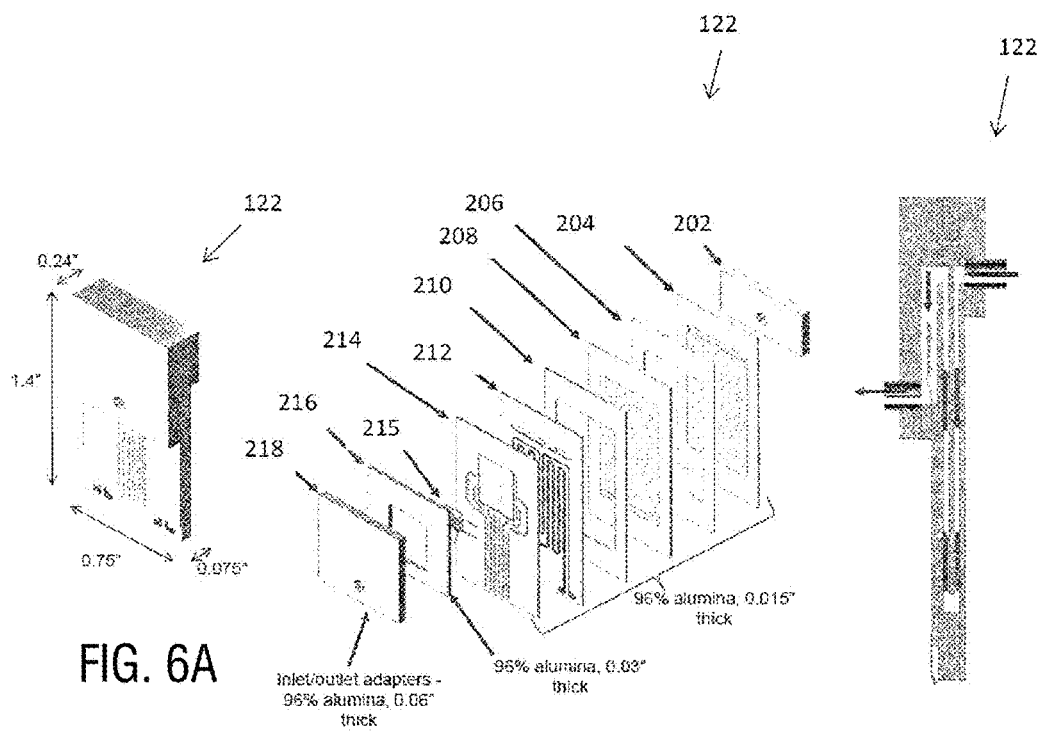
FIGS. 6A-6C illustrates one embodiment of a microchannel reactor and sensor assembly.

Referring to FIGS. 6A-6C, in one embodiment, the microchannel reactor/sensor assembly 122 can include a stack of thin plates adhered together. As shown in FIG. 6B, the stack can include (in order of air flow) an inlet adaptor 202, a heater and resistance temperature detector (RTD) plate 204, a spacer 206, a PtY plate 208, another spacer 210, another heater and RTD plate 212, a sensor plate 214 that suspends a sensor 215, a sensor spacer 216, and an outlet adaptor 218. The plates can include spaces there between configured to control the flow of air. Thus, as shown in FIG. 6C, the breath sample can flow in through the inlet adaptor 202, down in the space provided between the plates that are coated with a catalytic material (here, PtY) along the gas path. The breath sample then passes up in a space provided between plates coated with a catalytic material before passing into yet another space provided between plates of the microchannel reactor/sensor assembly 122 where the sensor resides and the breath sample can interact with the electrode materials on the surface of the sensor 215, and ultimately through the outlet adaptor 218. In this embodiment, PtY plate 208 has an area of PtY located on both sides of the plate corresponding to the apertures in spacer plates 206 and 210. Similarly, heater/RTD plates 204 and 212 each have an area of PtY located on one side of the plate corresponding to the apertures in spacer plates 206 and 210.

Figure 4:
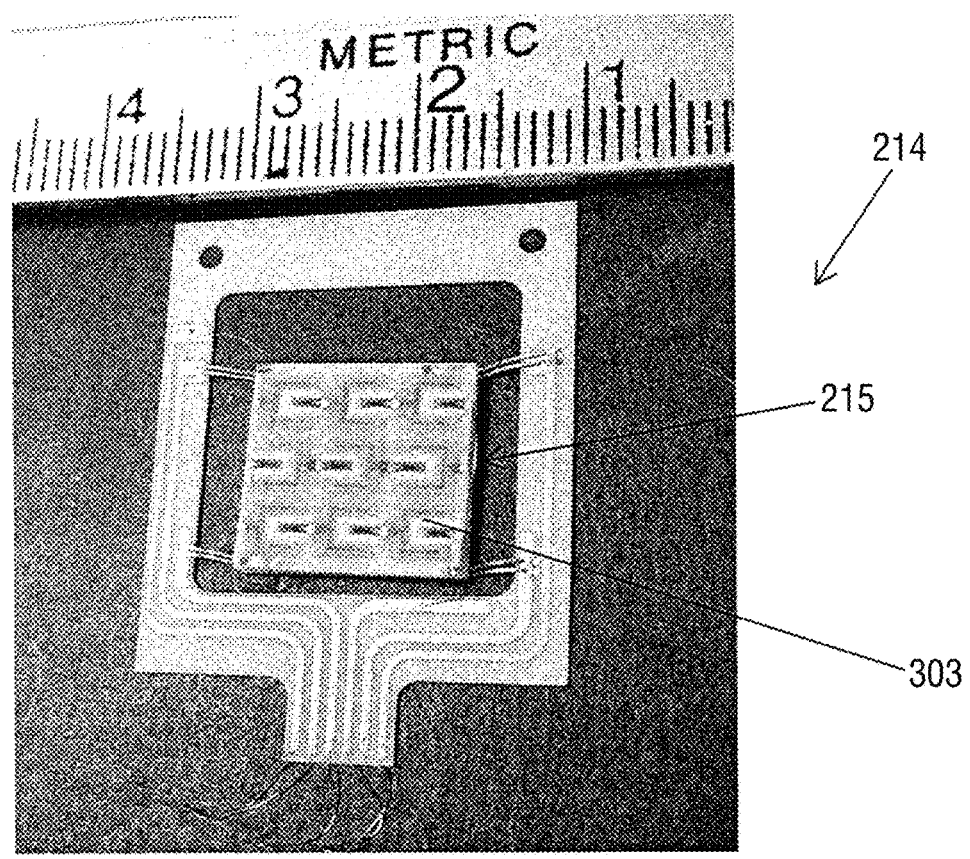
FIGS. 4 and 5A illustrate one embodiment of a sensor plate.

As show in FIG. 4, sensor 215 is suspended within an aperture in the sensor plate 214. Sensor 215 can include a substrate and a plurality of sensors 303, each sensor 303 including two electrodes (the sensing potentiometric electrode and the reference potentiometric electrode). In this embodiment, there are nine sensors 303 connected in series. In some embodiments, the range of ratios of electrode material surface areas can be between 1:1 and 5:1, such as approximately 3:1. A ratio within this range can advantageously ensure that the sensor is configured to measure NO in the parts-per-billion (ppb) range as well as minimize the level of signal conditioning required to get the NO result in the ppb range of interest (3-500 ppb).

Figure 5A:
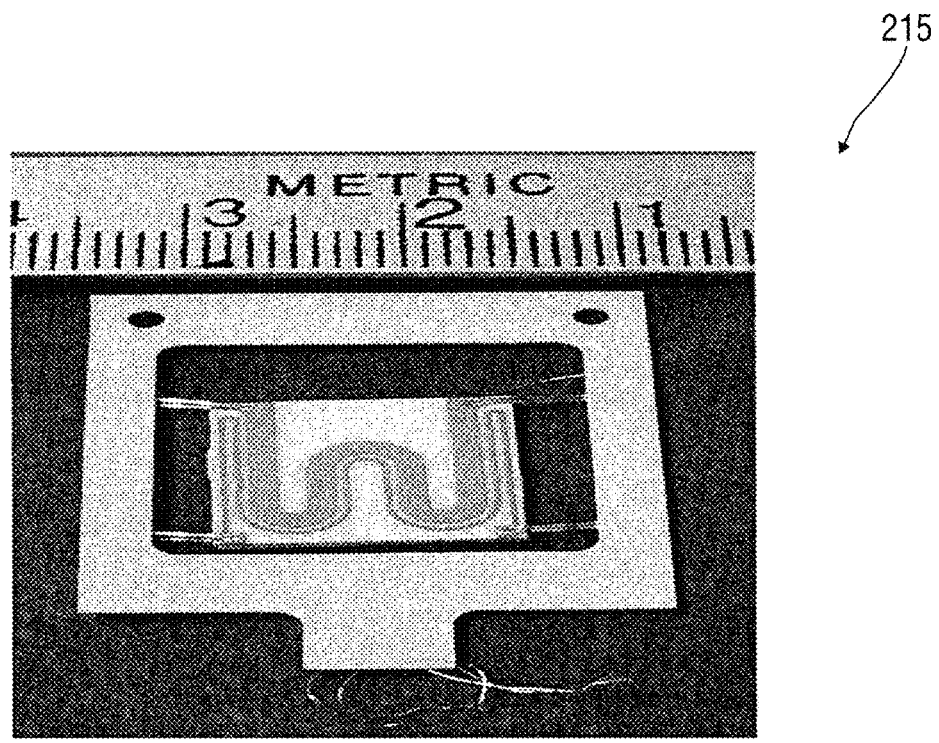
Figure 5B:
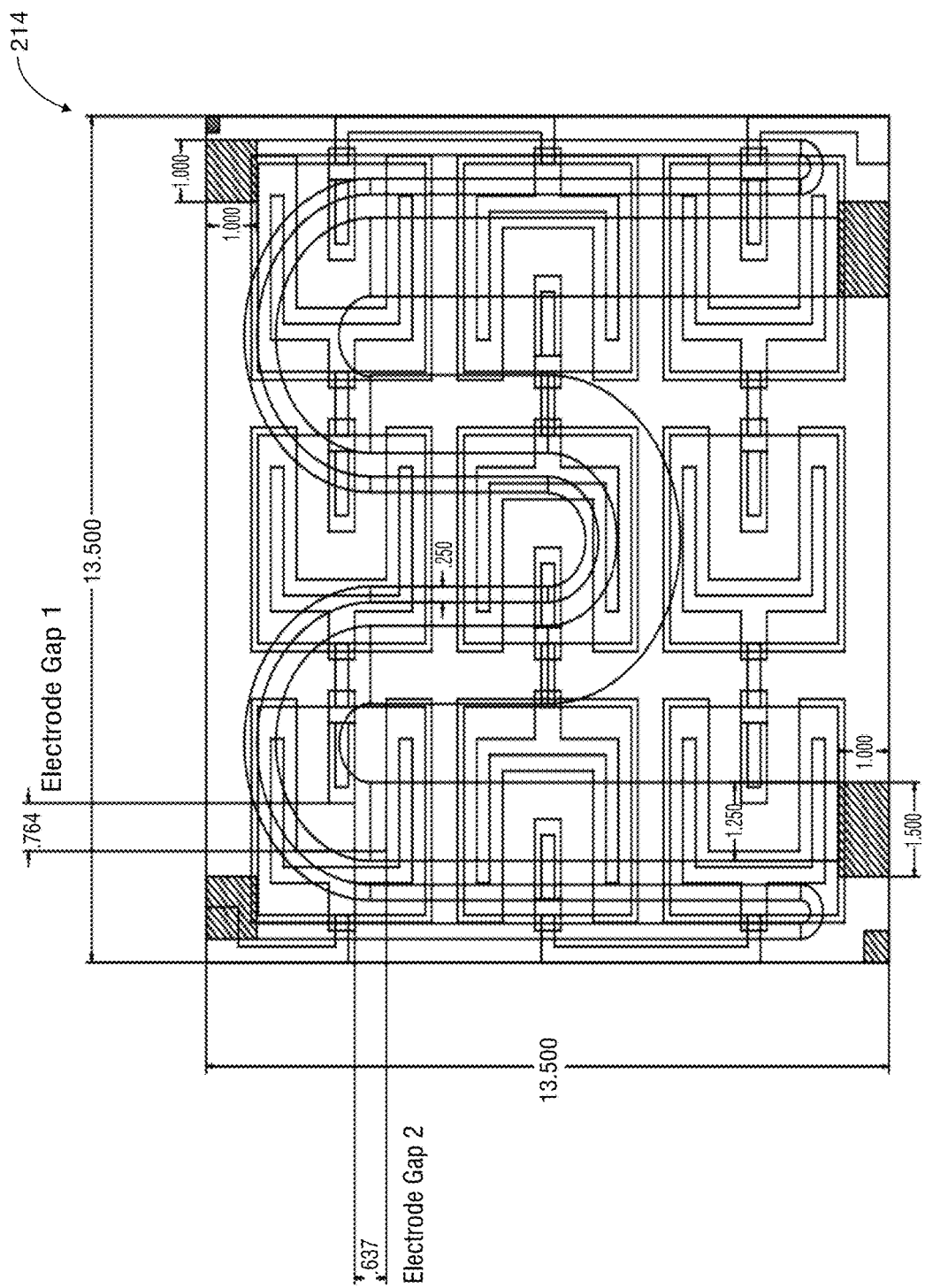
FIG. 5B illustrates one embodiment of a sensor.

Referring to FIGS. 5A-5B, the sensor 215 can also have a heating element and RTD element formed on the back side of the sensor substrate (or within the substrate), opposite from sensor elements 303. The heating element and RTD element may be formed into serpentine shapes and built into the sensor substrate (e.g., the substrate can be a co-fired ceramic). The heater and RTD plates 204, 212 can also have their heating elements and RTD elements formed into serpentine shapes as shown in FIG. 6B. In this embodiment, plates 204 and 212 are identical, each have a heating element and RTD element on one side (as seen on plate 212 in FIG. 6B) and PtY deposited on the opposite side (as seen on plate 204). The imbedded serpentine heater and RTD elements can advantageously provide preferred heat distribution through the plates of the microchannel reactor sensor assembly and provide precise detection and control of the heat differences on the plates of the microchannel reactor sensor assembly.

As shown in FIGS. 4-5B, the sensor and integrated heater can be suspended within microchannel frames to keep the heat conduction down. When the paths of heat conduction are minimized, the sensor with integrated heater can maintain a preferred heat distribution across the sensor array. The temperature of the sensor array is important for sensor performance and accuracy. The suspended architecture with high resistance to heat conduction means that only the sensor substrate is heated, thus reducing the amount of power required to bring the sensor to target temperature. Controlling the power budget is important for maintaining battery operation and thus portability of the device.

Advantageously, by having the microchannel reactor and sensor 122 assembly set up as a series of plates as describe herein, the ratio of surface area of PtY exposed to the volume of air sample is maximized. Further, using plates can allow the microchannel reactor/sensor assembly 122 to be relatively small, allowing the device 100 to be more easily portable, and reducing the energy needed to heat the air sample. In other embodiments (not shown), the microchannel reactor and sensor 122 assembly can be fabricated using other techniques to further miniaturize the assembly. For example, various material deposition (additive) and removal (subtractive) processes may be employed to create microchannel reactor and sensor assemblies having even smaller dimensions. The assemblies can be built up layer by layer using chemical vapor deposition (CVD), physical vapor deposition (PVD), electrodeposition, electroless deposition, or the like. In some embodiments, voids for air flow, such as those shown in FIG. 6C, can be formed by creating sacrificial layers which are later dissolved after they have served as a substrate for layers added on top of the sacrificial layers.

Figure 2:
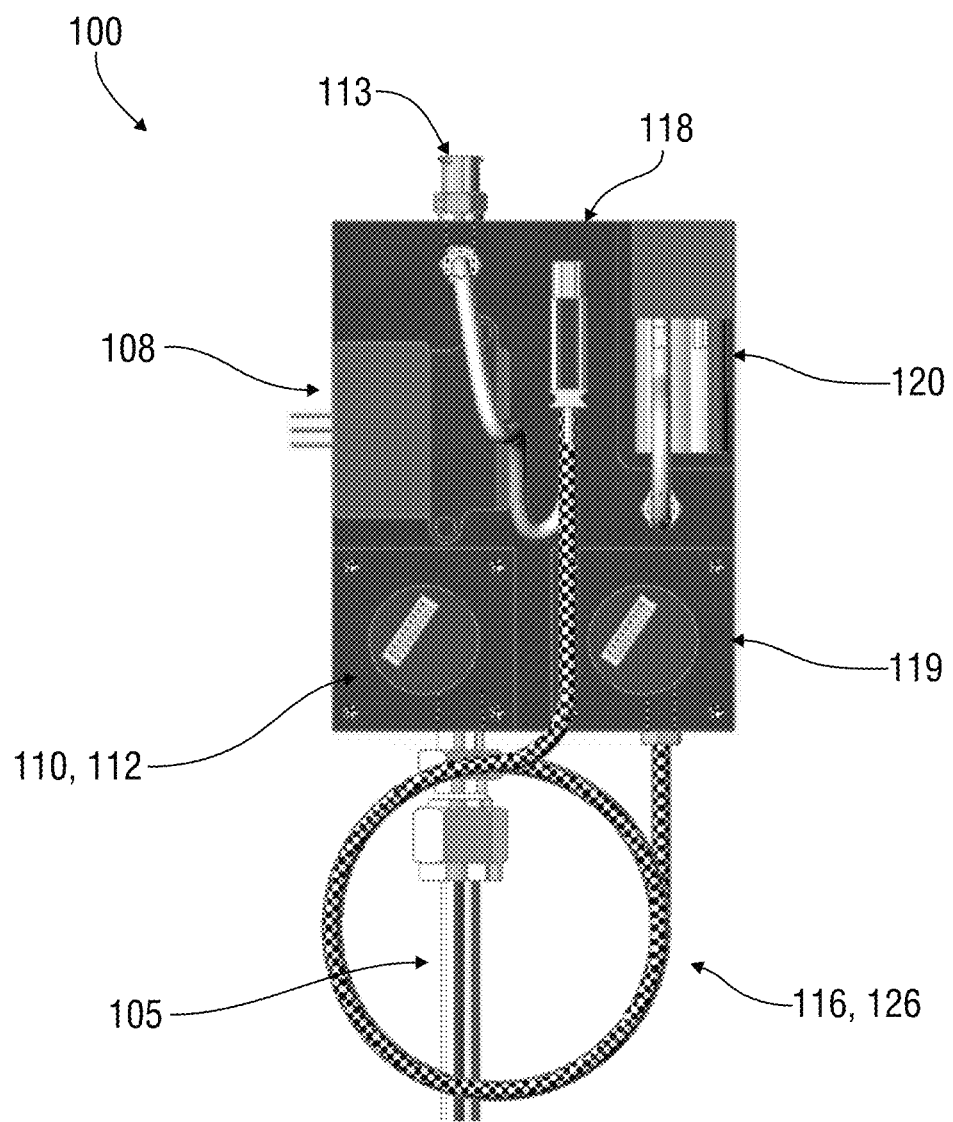
FIGS. 2-3 is a layout of one embodiment of an NO detection device.
Figure 3:
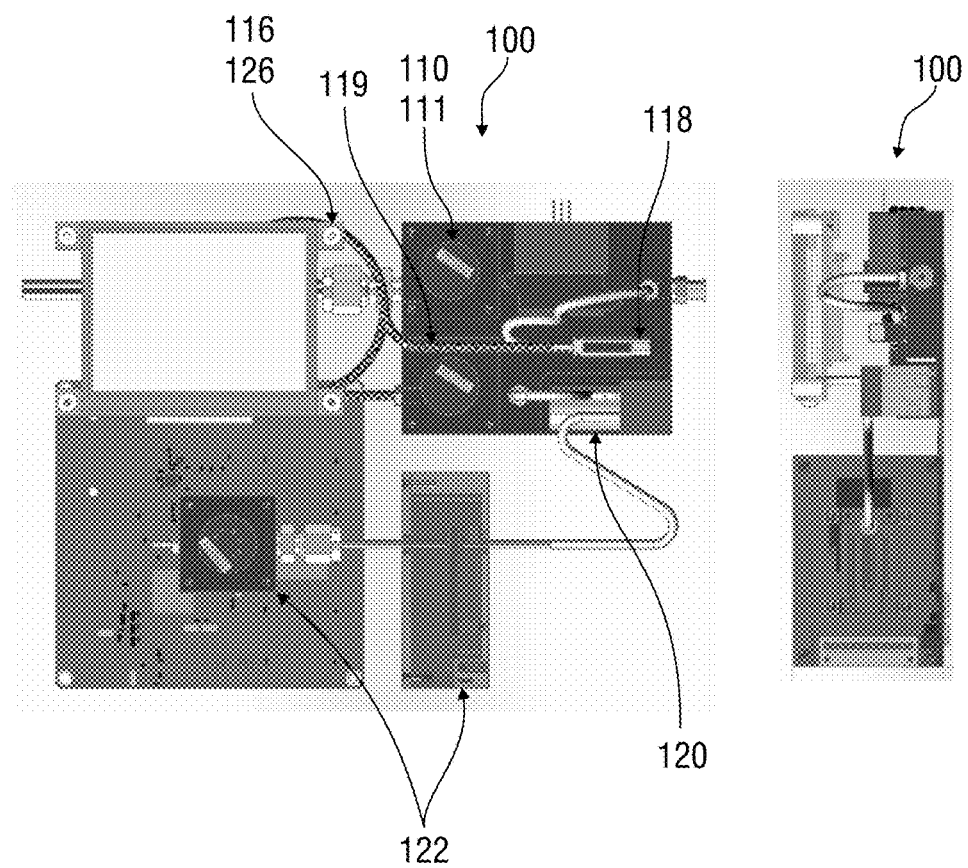

Referring to FIGS. 2-3, the layout of the device 100 can be compact to ensure portability. For example, in one embodiment, the detection box 104 can be 8" by 2" by 6.5". The relatively flat design can allow for the maximization of distance between the heated components (microchannel reactor/sensor) and the non-heated but heat sensitive components (battery and PCB board). Since the components in the "flat layout" are not stacked on top of each other, this reduces the volume of the device, which allows for efficient heat dissipation.

The device 100 can be configured to precisely control the important variables, such as humidity, temperature, pressure, and flow rate. For example, the humidity can be controlled using the first and second humidity sensors 110, 119. The first humidity sensor 110 can detect the amount of humidity that is coming into the device 100 from the patient's breath through the mouthpiece 102. The second humidity sensor 119 can detect the amount of humidity once the breath transverses the humidity control system into the microchannel reactor/sensor 122. If the humidity level at the second sensor 119 is equal to or greater than that at the first sensor 110, this may be indicative of a fault in the system. Accordingly, a controller can signal an error. The humidity at the second sensor 119 should be substantially equal to ambient conditions and controlled tightly to the ambient humidity level, such as to have a humidity within 2% of ambient. This control ensures that the humidity level that is going into the microchannel reactor sensor assembly is substantially constant during the duration of a measurement.

Further, the temperature difference of the catalytic converter and the sensor can be controlled by the RTD or RTDs to be within about 100-300 degrees Celsius, such as about 200 degrees Celsius. Precise control of this temperature difference is important in some embodiments, as the higher the temperature difference, the greater the signal. In use, the catalytic converter should operate above 200 degrees Celsius in order to maintain reaction efficiency while the sensor should operate in excess of 350 degrees Celsius to activate oxygen conduction within the sensor electrolyte material. Further, in some embodiments, temperatures above 950 degrees Celsius at the NO sensor could be too high for the device to function properly while temperatures below 200 degrees Celsius at the reactive filter could be too low for the catalytic reactive filter to function efficiently. In one embodiment, the desired temperature difference is achieved by ensuring that the electronics keep the temperature of the reactive filter and the temperature of the sensor nominally at 250 degrees Celsius and 550 degrees Celsius, respectively.

The flow sensor 108 and pressure sensor 112 can be used to trigger the 3-way control valve 118 to toggle and pull from the breath sample line rather than the ambient line, thereby feeding the breath sample over the microchannel reactor/sensor assembly to perform the $NO_x$ measurement. In some embodiments, the target flow rate is 3 L/min (+/−10%). Likewise, pressure sensors can look for a pressure of 5 to 20 cm of $H_2O$. If either of the flow rate or the pressure range is not met, the 3-way control valve 118 can be configured not to toggle, and as such, the NO sensor will not measure NO in the patients breath. In some embodiments, the pressure and flow sensors 108, 112 can also be used to provide feedback to the user regarding the pressure and/or flow so as to help the user provide the necessary pressure and/or flow for activation of the NO measurement. Further, in some embodiments, the user is required to meet both the pressure and flow rate goals continuously for a total of less than 15 seconds, such as approximately 10 seconds, in order to obtain the NO reading.

In some embodiments, by controlling all of these variables, the accuracy of the resulting NO reading can be within +/−10 ppb, such as within +/−7 ppb or within +/−3 ppb.

Figure 7A:
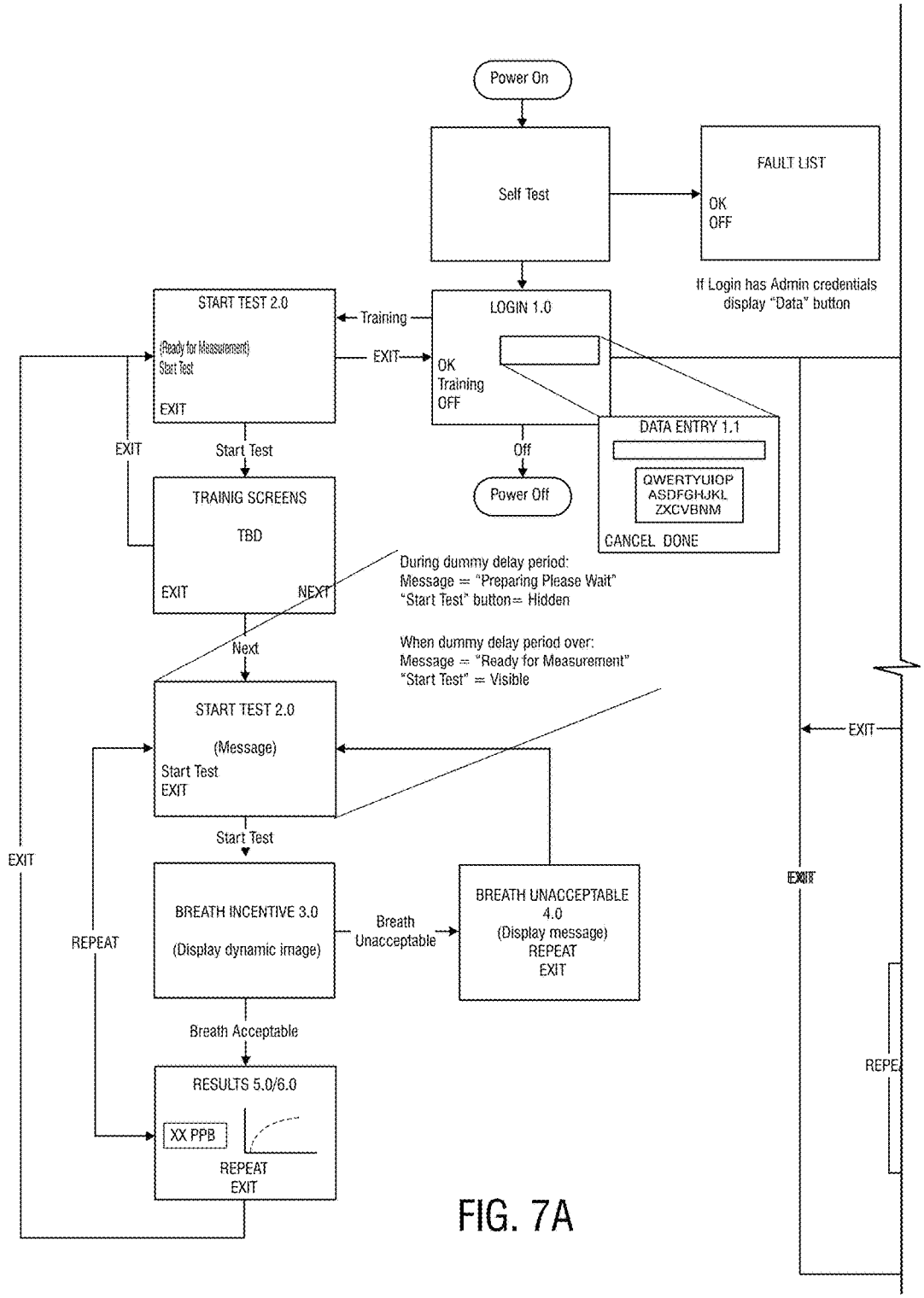
FIGS. 7A, 7B, and 7C are schematics illustrating one embodiment of a user interface.
Figure 7B:
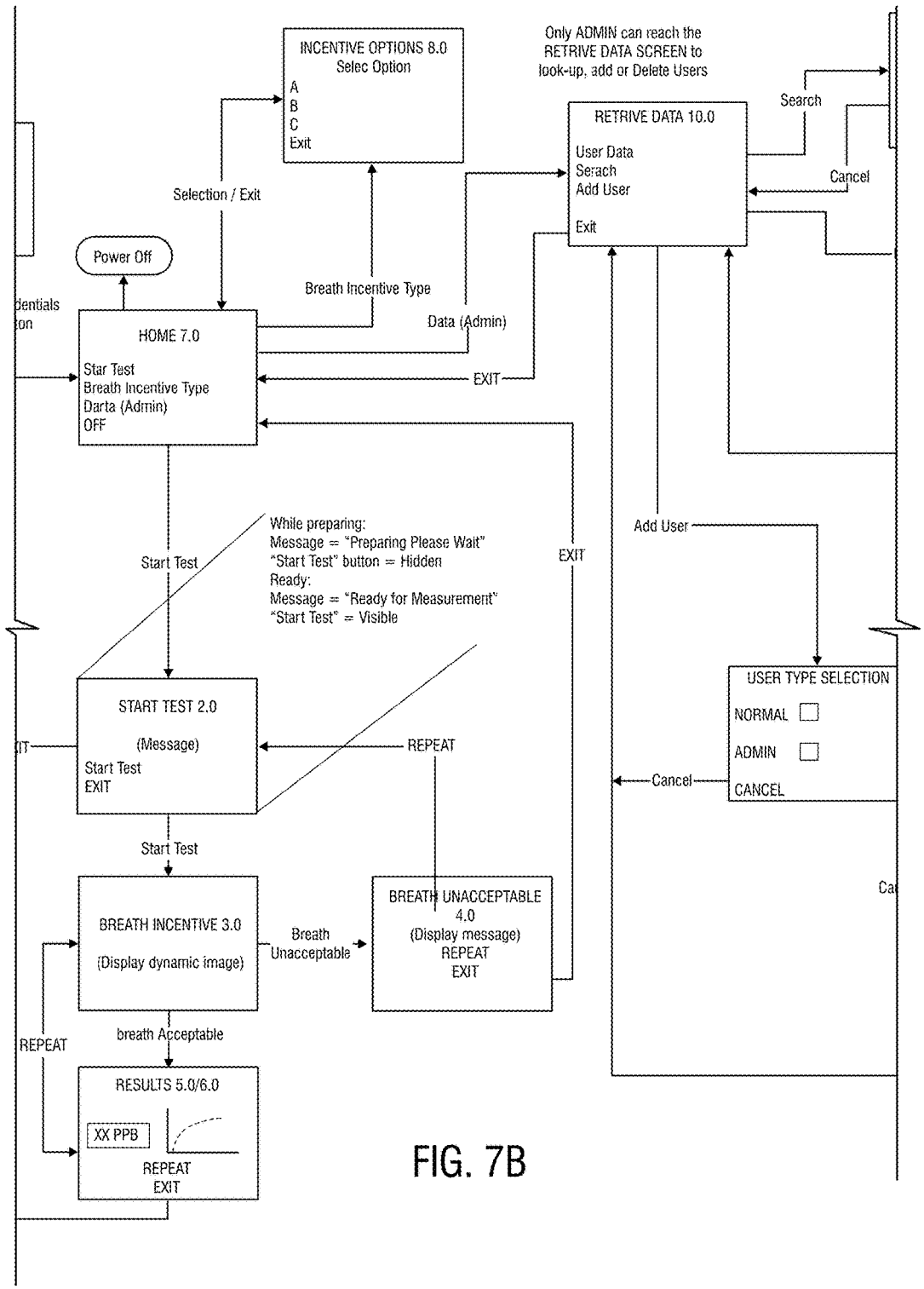
Figure 7C:
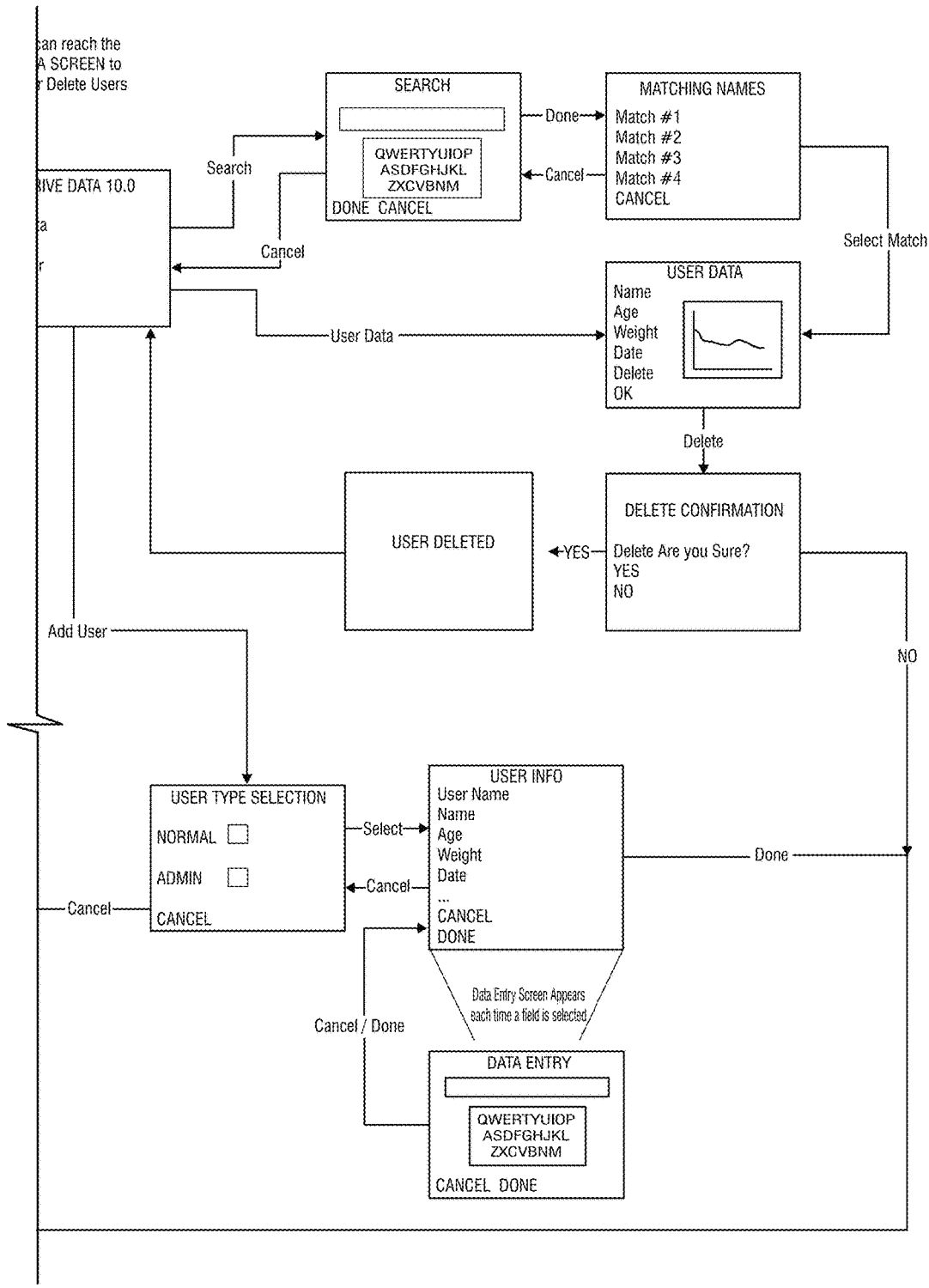

Referring to FIGS. 7A, 7B, and 7C, in some embodiments, a user interface can be provided to give the patient visual, audible, and/or tactile feedback as to the variables and/or results of the system.

In some embodiments, the device 100 is calibrated using electronics coupled to the microchannel reactor and sensor. To do so, the heating parameters for each reactive filter and sensor assembly can be uploaded to the device when the micro-channel reactive filter and sensor assembly is plugged into the device. The microchannel reactive filter and sensor assembly (MCRS) can also provide the calibration curve parameters to the device. This is how the device interprets whether a measured potential from the sensor is equal to a specific NO concentration. A sample calibration curve is shown in FIG. 8.

The detection system 100 can be a flow-through device in that air (either from the ambient through inlet 124 or from the breath at mouthpiece 102) can continuously flow into and out of the system. That is, the amount of air into and out of the system at any one time can be controlled. Having a controlled and continuous flow of ambient air through the device before and after the user's breath can advantageously set a reliable baseline for NO measurement. Further, by providing analysis of the breath via continuous airflow (i.e., without storing the breath), the NO reading can be provided quickly and efficiently. For example, the system can provide the NO reading in less than 15 seconds from when the user begins to breath into the device.

The flow rate through the mouthpiece can be regulated to 3 L/min (+/−10%). The flow through the catalytic converter and NO sensor can be in the 0.01 to 1 L/min range, such as 0.2 L/min. The power needed to heat the MCR can be 2-9 Watts. The mass of the reactive filter (catalytic converter) can be within 2-200 grams. The external dimensions of the microchannel reactive filter and sensor assembly in this embodiment are nominally 0.75 inch×1.25 inch×0.5 inch. The variation for the temperate at the converter can be less than +/−2 degrees Celsius. The efficiency of the converter can be >90% to ensure proper performance of the sensor.

As described above, pulmonary function tests typically require different machines for conducting different tests. For example, the large delta between the breath flow rates for spirometry and FeNO measurements has previously prevented use of a single mechanism to make the measurements. In the embodiment illustrated below, multiple markers, such as spirometry and eNO tests, can be measured and tracked in a single device mediated by airflow-restriction mechanism. Other pulmonary function tests or gas sensors may be employed in the device illustrated.

In one embodiment, a monitoring device is contained in a housing that contains an inlet section, a measuring section and a flow detection component. In addition, the device contains an adjustable airflow restriction component and at least one gas detection sensor. The inlet section receives a gaseous sample from a subject, e.g., a subject, or source, that expels air into the inlet section, which then proceeds downstream into the device according to variable restrictions that alter the speed and path of the gaseous sample expelled from a subject into the device. In the embodiment illustrated, an inlet section is positioned in the housing and configured to receive a gaseous sample. A measuring section is positioned adjacent to the inlet section and connected via a hole in the inlet section. A flow detection component is positioned in the inlet section and configured to measure the flow rate of a gaseous sample entering the inlet section. Positioned upstream of the flow detection component is an airflow restriction component. An adjustable partition can also be positioned downstream of the flow detection component, which can be adjusted to further direct and restrict airflow. At least one gas detection sensor is positioned in the measuring section.

As indicated above, the lung-function monitoring device comprises two sections for collecting and sensing a gaseous sample from subjects. An inlet section is composed of an inlet port or channel having an orifice at one end that extends axially along an airflow path to the opposite end, which incorporates an airflow restriction component, such as a shutter-controlled aperture. A disposable or easy-to-sterilize mouthpiece can be adapted to the orifice opening to allow for directing airflow into the inlet section. When performing a spirometry test, for example, a user blows air into the device via a mouthpiece to an inlet port where a gaseous sample can flow through a flow detection component, such as an impeller-based flow meter, and exit the inlet section via an opposite opening that exits the device. Conversely, when performing eNO test, a user steadily exhales breath into the inlet section with the airflow restriction component in a restricted position, which consequently re-routes the gaseous sample to the eNO detector contained in the sensing section. To further close off an airflow out of the device, a movable partition on the back of the housing can be moved to a closed position during this test to further retain and re-route the gaseous sample through the hole and into the measuring section. At least one gas sensor, e.g., such as the NO sensor described above, is placed along a sensing compartment.

Figure 9:
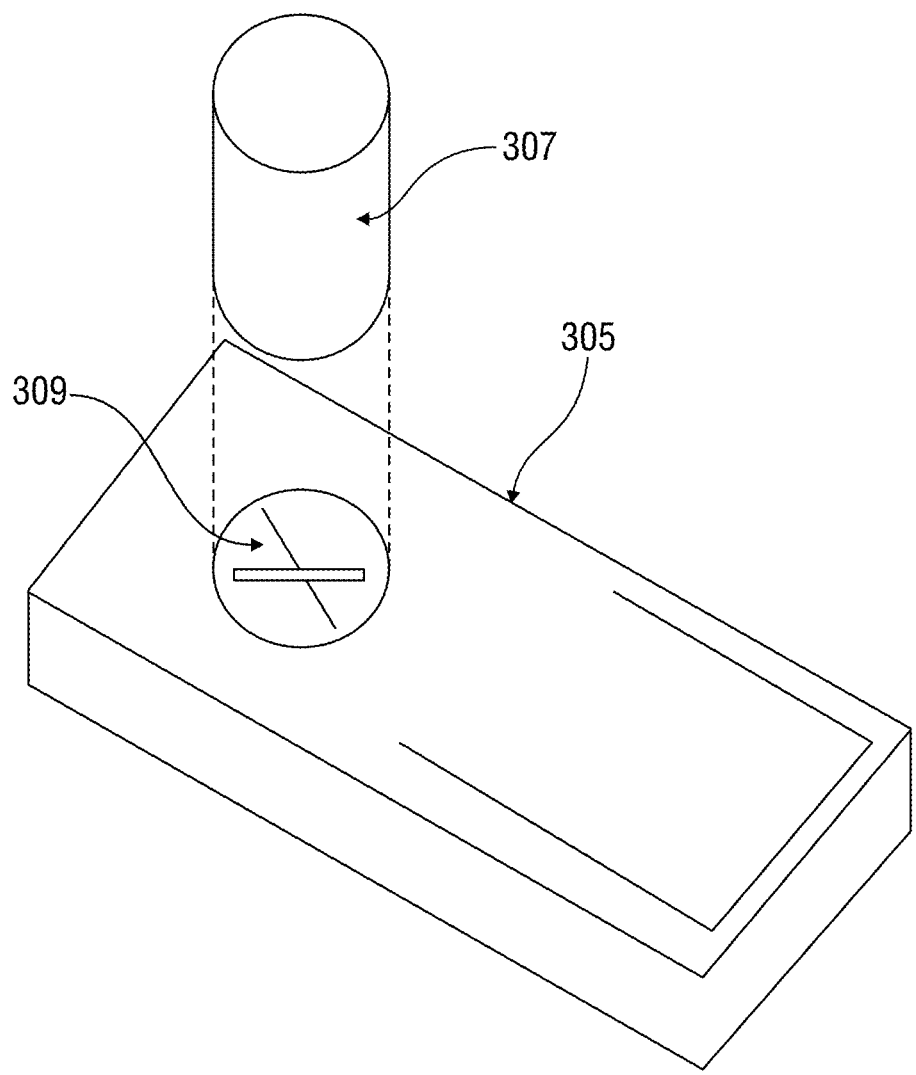
FIG. 9 illustrates a perspective view of one embodiment of the present monitoring device.

To further illustrate the invention, reference is made to the drawings that are directed to one embodiment of the present invention. Referring to FIG. 9, an example of the monitoring device housing 305 is shown. The housing is preferably designed such that it can be hand-held and portable. The housing further contains an inlet section containing an impeller assembly 309. A mouthpiece 307 is shown which can be attached to the device for directing airflow into the inlet section containing the impeller assembly 309. The mouthpiece can be of any suitable shape and made of any suitable material as long as it allows for the exhaled breath of a user to be directed into the inlet section of the device. The mouthpiece may be disposable, or made of a material that is easily sterilized.

Figure 10:
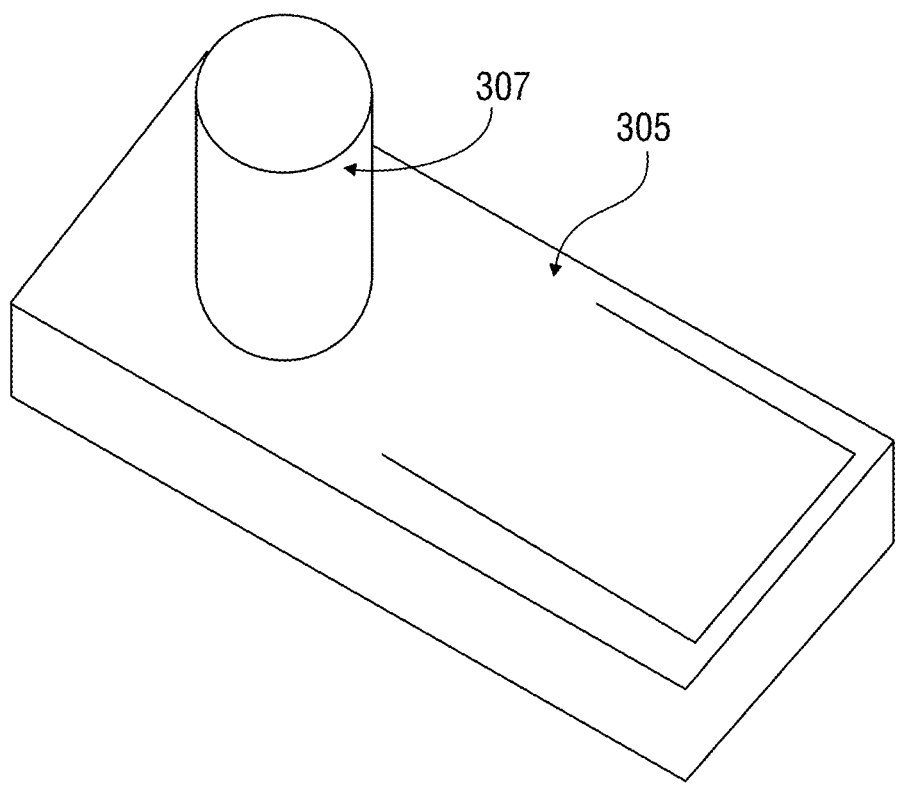
FIG. 10 illustrates a perspective view of one embodiment of the present monitoring device with one embodiment of a mouthpiece assembled onto the monitoring device.

Referring more specifically to FIG. 10, the mouthpiece 307 is shown attached to the monitoring device 305. By way of example and depending on the desired test, a subject expels a gaseous sample, e.g., air from the lungs, into the inlet port via the mouthpiece. A flow detection meter positioned in the inlet and situated along the flow path measures the gaseous sample. In a preferred embodiment, the flow detection meter is an optical-impeller based flow meter that optically counts impeller revolutions.

Figure 11:
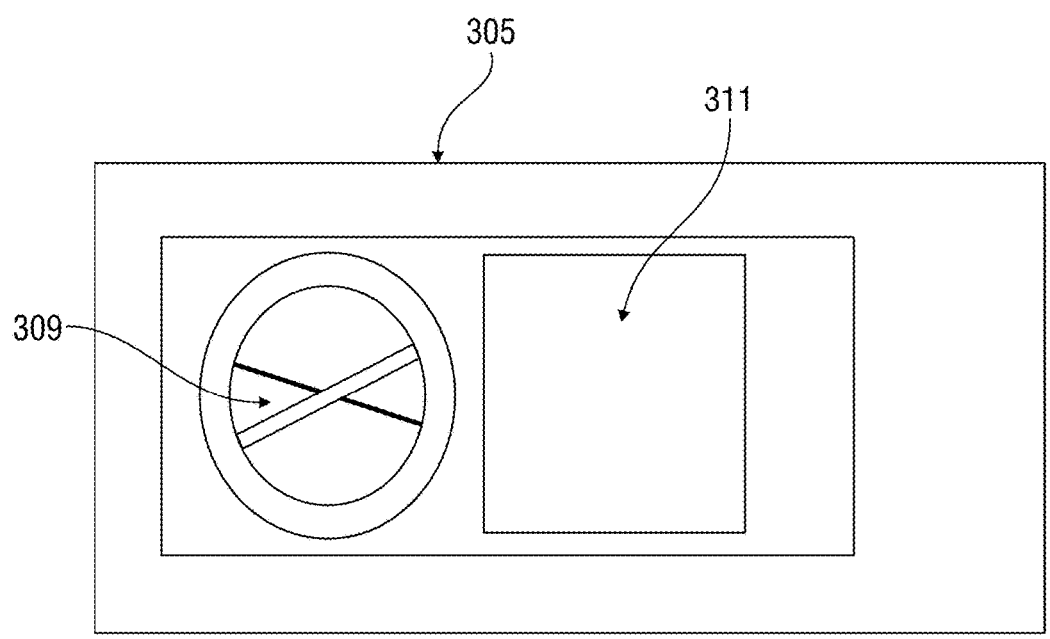
FIG. 11 illustrates a plan view of the back of one embodiment of the monitoring device showing the device in the open partition position.
Figure 12:
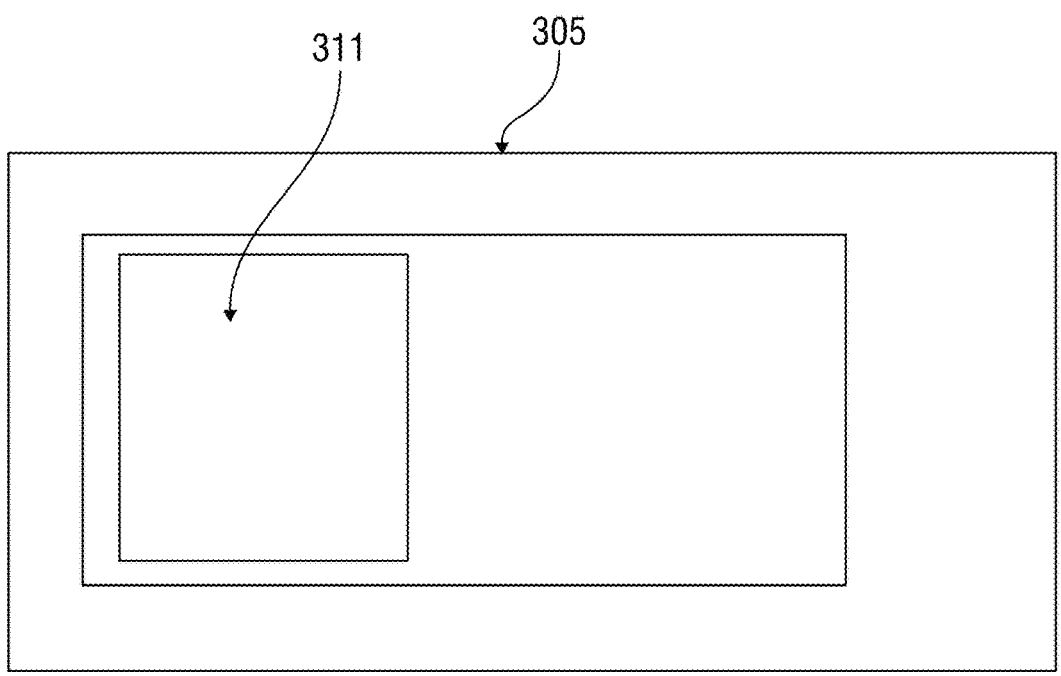
FIG. 12 illustrates a plan view of the back of one embodiment of the monitoring device as illustrated in FIG. 11 showing the device in the closed partition position.

Referring to FIGS. 11 & 12, the monitoring device is illustrated showing a movable partition 311 positioned on the back of the monitoring device housing. In this embodiment, the movable partition can be adjusted to further alter the airflow path in the device to enable the device to be employed for different tests. For example, the movable partition can be adjusted to a fully open position, as shown in FIG. 11. In this position, expelled breath from a subject can pass directly through the device, allowing, for example, a spirometry test that requires a subject to expel breath forcefully into the device. In another example, the movable partition can be adjusted to a fully closed position, as shown in FIG. 12. In this position, air expelled by a subject into the device will be routed along an alternate path, for example, to a sensing area. In such a closed position, the device can be employed in measuring eNO where a user expels breath at a slow and steady rate into the device. In addition, the movable partition can be adjusted to any position between fully open and fully closed to accommodate other test requirements.

Figure 13:
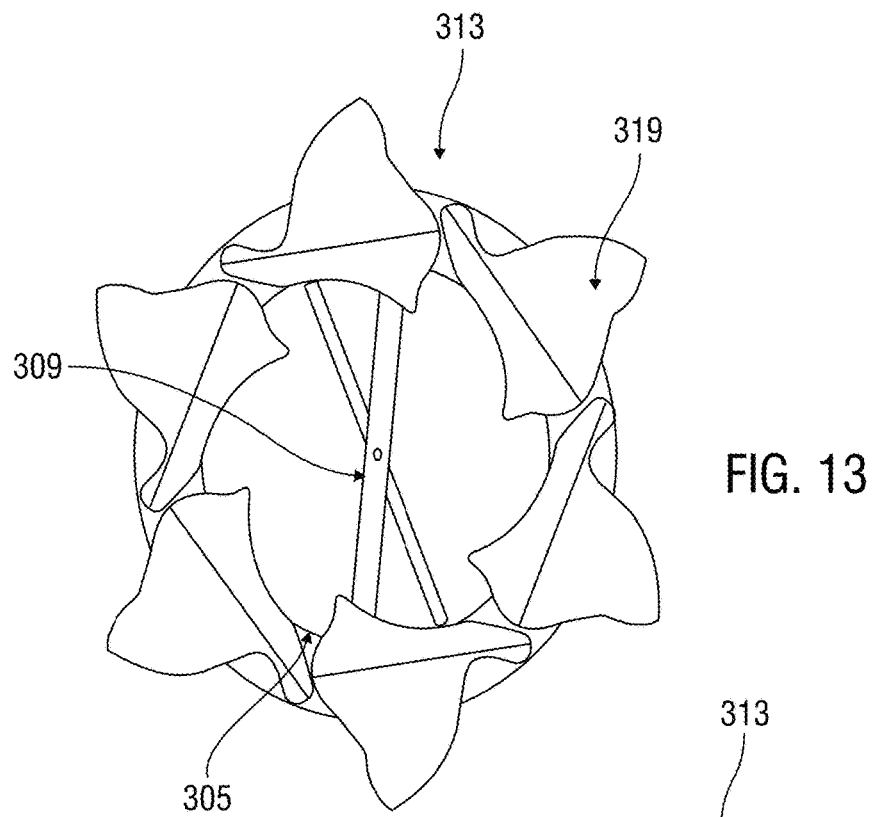
FIG. 13 illustrates a plan view of one embodiment of the impeller-shutter assembly of the present monitoring device.
Figure 14:
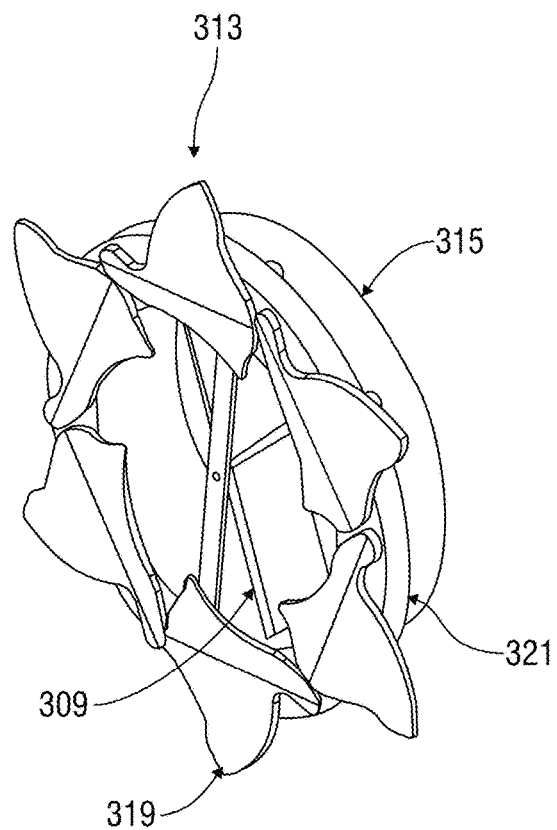
FIG. 14 illustrates a perspective view of one embodiment of the impeller-shutter assembly as shown in FIG. 13.
Figure 15:
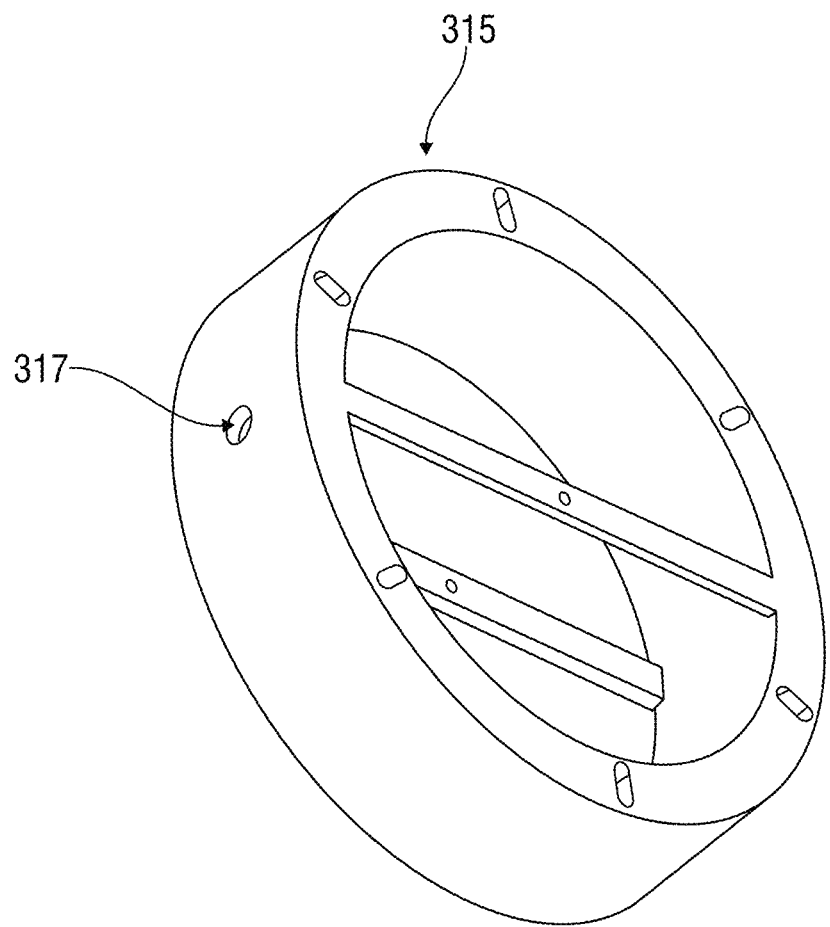
FIG. 15 illustrates a perspective view of one embodiment of the impeller shell.

Referring to FIGS. 13 & 14, one embodiment of an impeller-shutter assembly 313 is illustrated. The impeller assembly 309 is shown housed in an impeller-shutter assembly 313 and forms part of the flow meter, which includes the impeller assembly, sensing elements, such as one or more optical sensors, and an impeller shell 315. Referring more specifically to FIG. 15, the impeller shell 315 is illustrated with hole 317, which allows for airflow communication between the inlet section and the measuring section.

In the embodiment illustrated, the impeller assembly of the flow meter requires a certain amount of air flowing into the device to cause the impeller assembly to spin. At a very low flow rate, the impeller will not spin, or will spin erratically. When a subject forcefully expels air into the device for certain measurements, e.g., a pulmonary function spirometry test, a gaseous sample flows through the impeller, causing it to rotate. In a typical spirometry test, the airflow can range from 100 to 700 LPM. The air then exits at the opening end of the shutter-controlled aperture. The amount and speed of air passing through the impeller can then be detected by sensing means along the impeller assembly. In one embodiment of the present invention, the measured lung function parameters from the flow meter can be converted to signals and transmitted to a microcontroller integrated with the monitoring device.

Again referring to FIGS. 13 & 14, the impeller-shutter assembly 313 is shown with an airflow restrictor/shutter disposed upstream of the impeller assembly 309 along the airflow path extending from the inlet section. As shown in the embodiment depicted, the flow shutter comprises a multi-blade diaphragm comprising shutter blades 319. The aperture of the flow shutter can be adjusted to fully opened, closed or partially-opened positions to a desired degree to control the amount of the gaseous sample exiting the inlet section, allowing for different tests requiring different air flow speeds.

Figure 16:
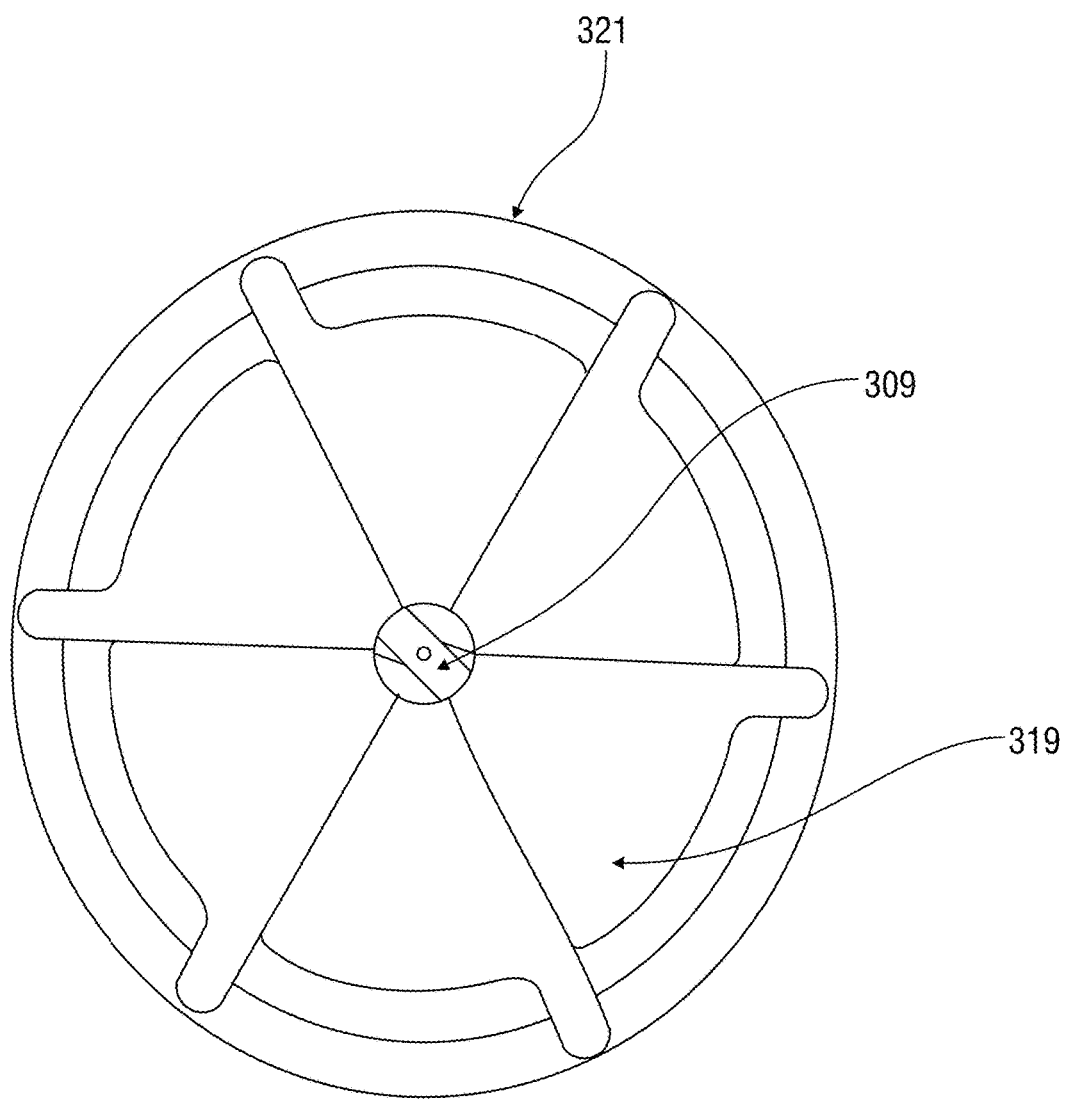
FIG. 16 illustrates a plan view of one embodiment of the retainer ring assembly of the present monitoring device.
Figure 17:
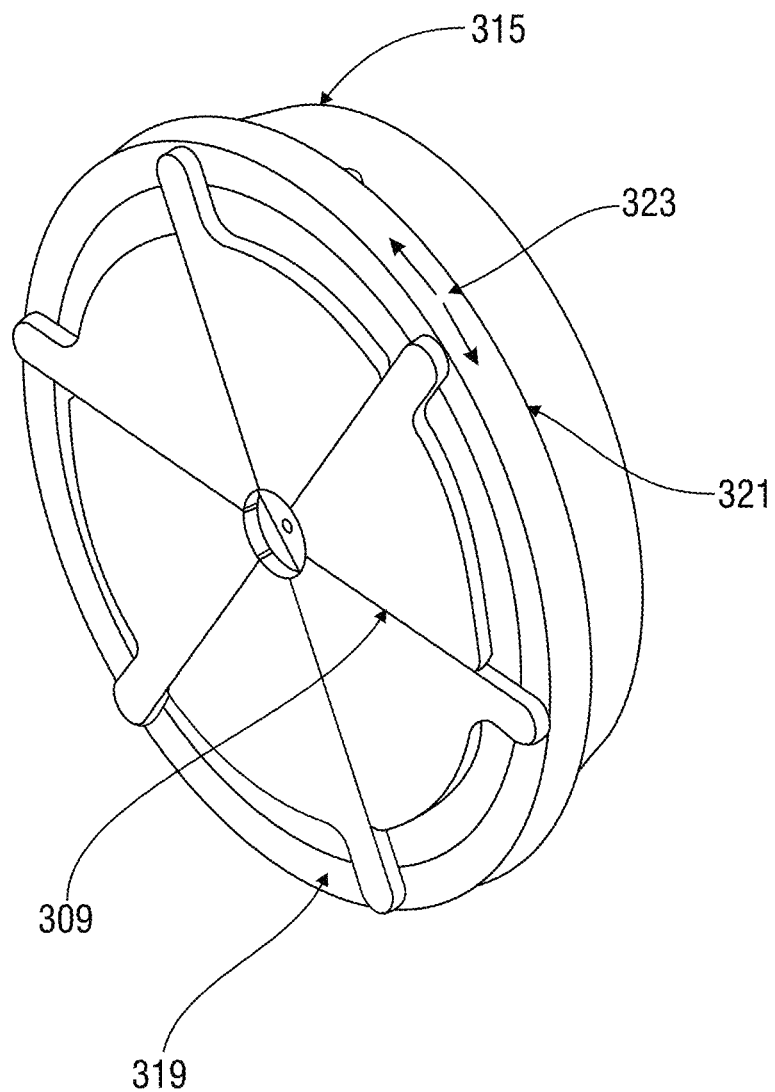
FIG. 17 illustrates a perspective view of one embodiment of the retainer ring assembly as shown in FIG. 15.

Referring more specifically to FIGS. 16 & 17, the opening dimensions of the flow shutter can be fine-tuned by an outer retainer ring assembly 321, which forms part of the impeller-shutter assembly 313. The dimension of the shutter opening is adjusted by rotating the ring 321 back and forth in the direction 323. The shutter opening can be controlled mechanically through manual manipulation or controlled electronically through, for example, integrating the rotation of the ring with a microcontroller integrated with the device.

When the flow shutter is fully open in response to manual control or to an electrical signal during a spirometry test, which requires a user to exhale forcefully, the open shutter allows the free flow of air entering the inlet section. Meanwhile, a flow rate can be measured by a flow meter.

Figure 18:
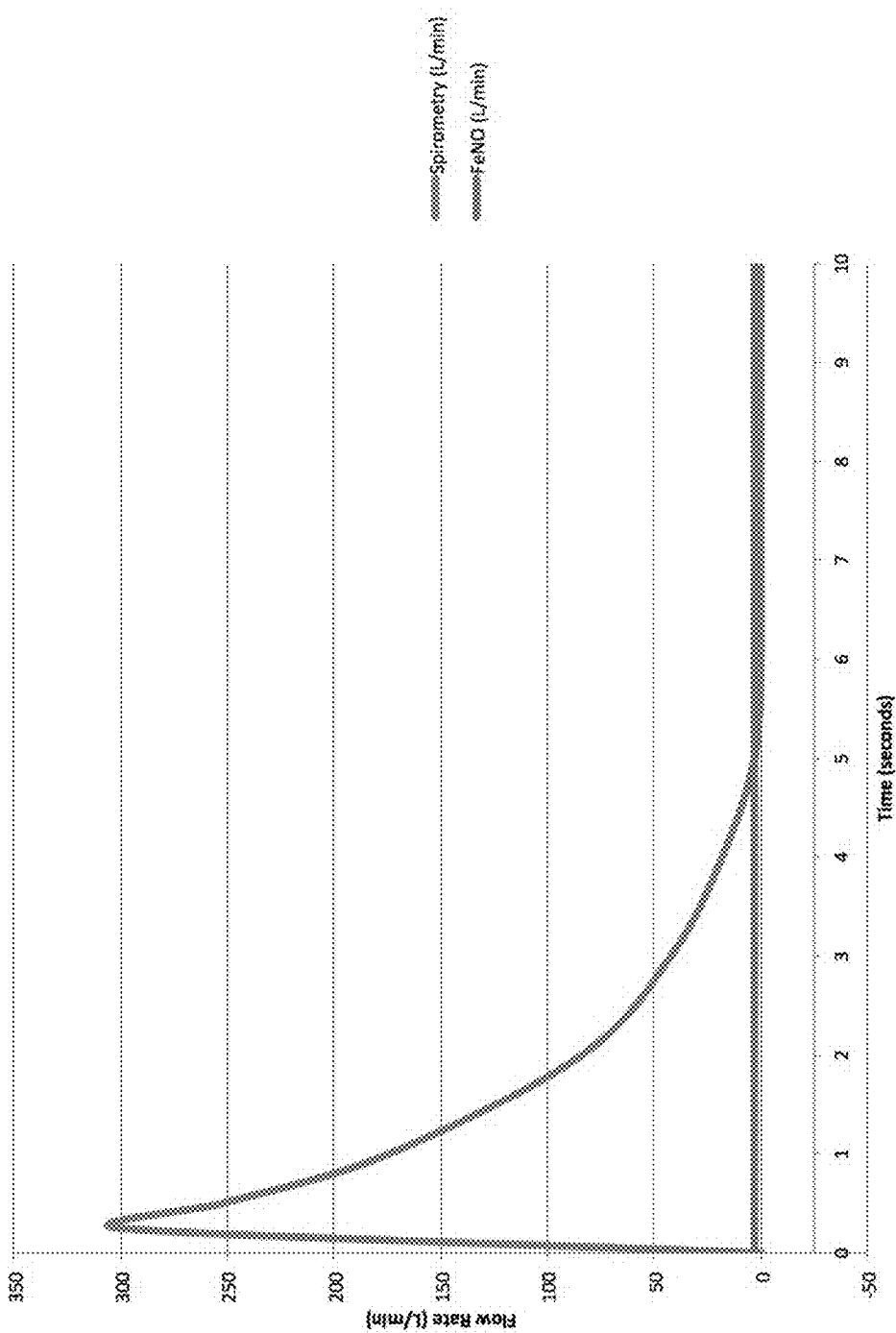
FIG. 18 is a sample chart illustrating flow rates against time for spirometry (PEF) and FeNO measurements.
Figure 19:
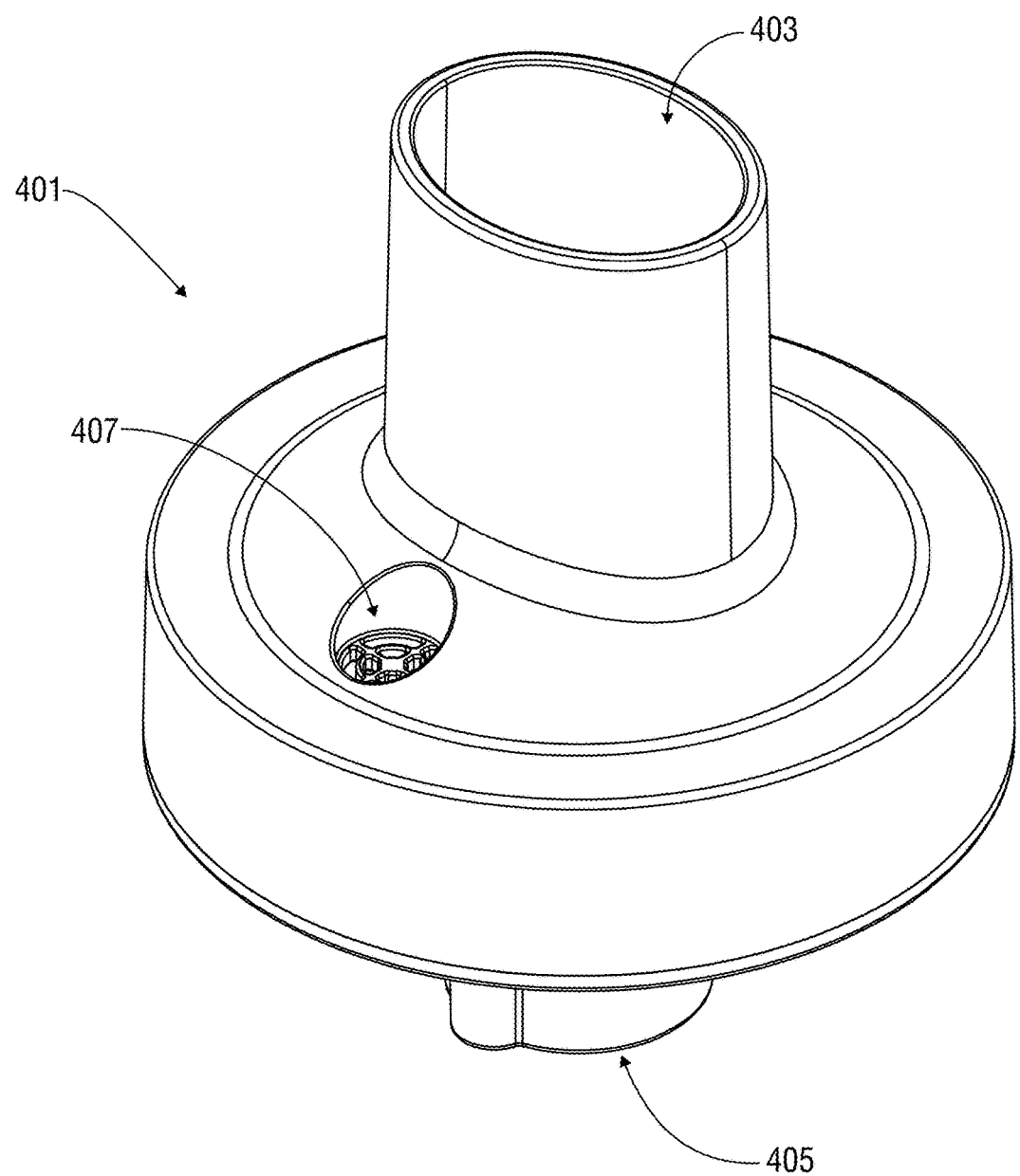
FIG. 19 is a perspective view illustrating one embodiment of multi-pathway mouthpiece.
Figure 20:
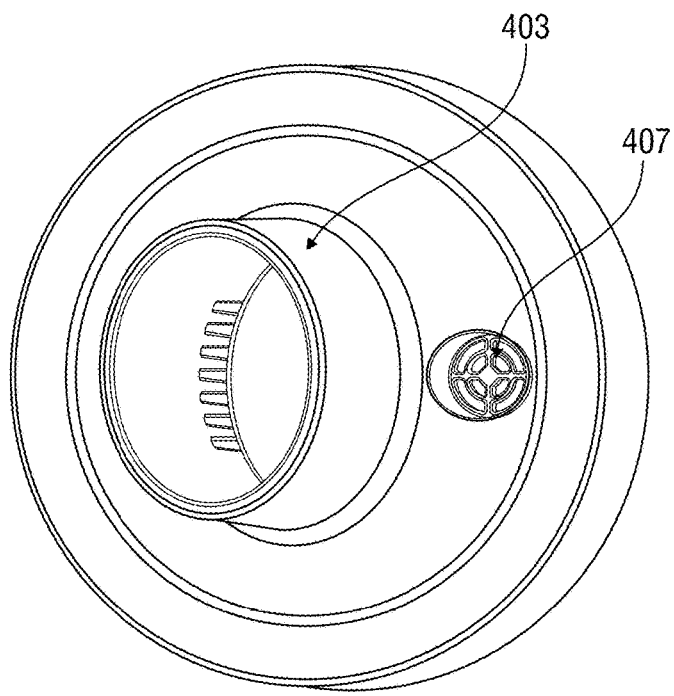
FIG. 20 is a perspective view illustrating the user side of one embodiment of a multi-pathway mouthpiece.
Figure 21:
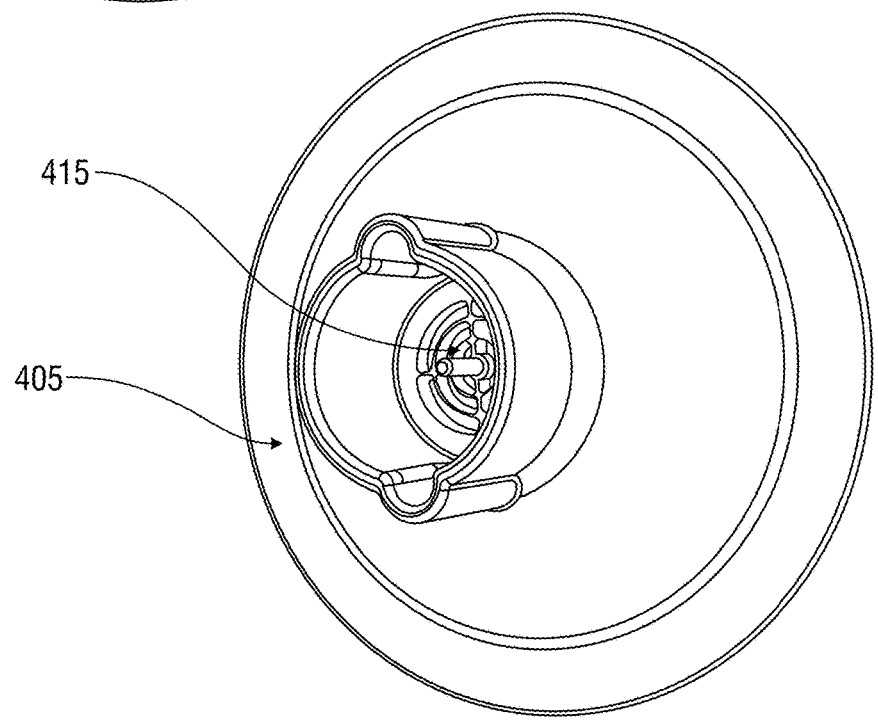
FIG. 21 is a perspective view of the device side of one embodiment of a multi-pathway mouthpiece.
Figure 22:
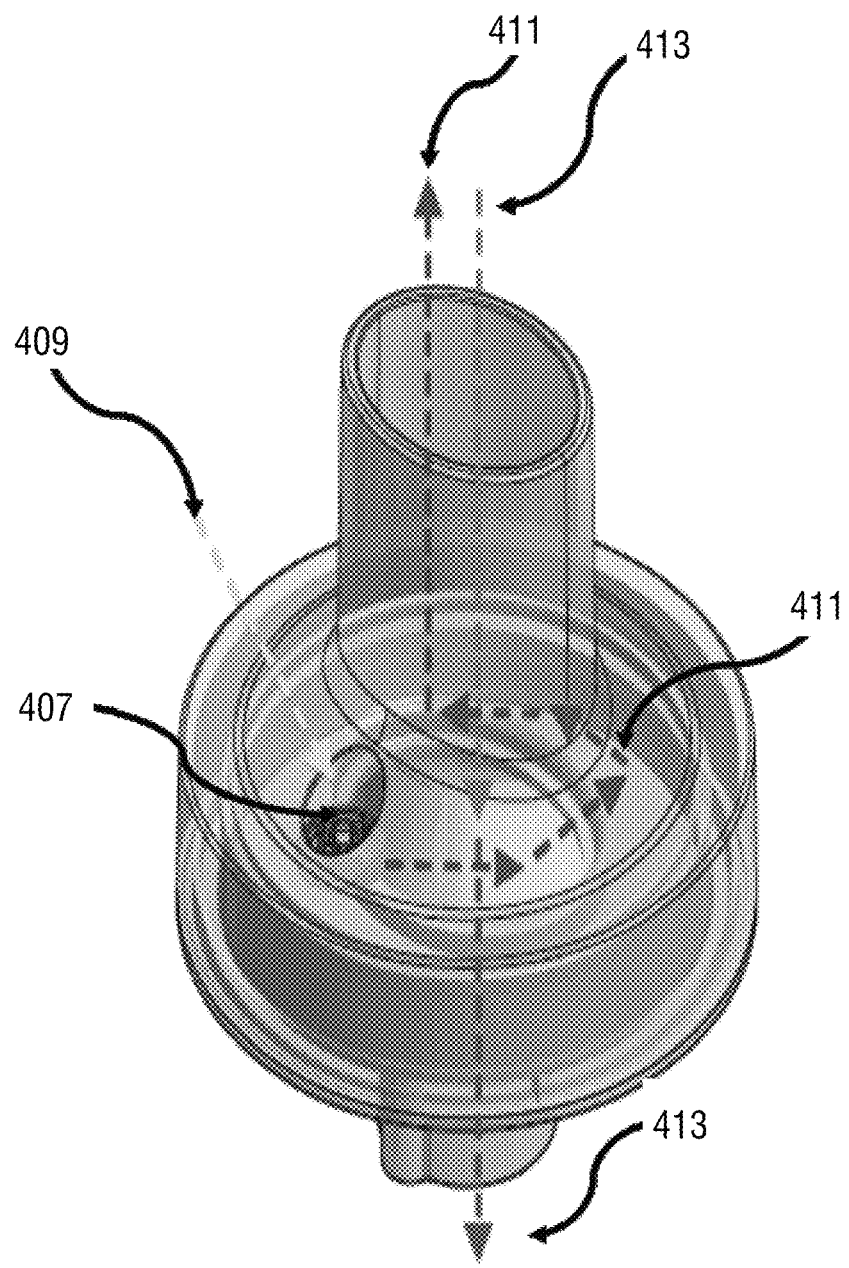
FIG. 22 is a perspective view of the airflow of one embodiment of a multi-pathway mouthpiece.

As described, the shutter-controlled mechanism of the present lung-function monitoring device allows measurement of gaseous samples requiring selected flow rates. For example, measurement of eNO concentration requires a steady flow of air, for example, of 3 to 5 LPM over a period of about 10 seconds. To conduct this test, the aperture of the shutter assembly is adjusted manually or electronically to achieve a predetermined flow rate. The closed exit of the inlet section results in redirecting the inflow of exhaled breath to the contiguous sensing section coupled with at least one NO sensor contained in the sensing section to measure the level of NO in exhaled breath. As illustrated in FIG. 18, the adjustability of flow rates into the device allows for multiple tests in one device that require vastly different flow-rate conditions. For example, spirometry flow rates reach into the hundreds of liters per minute and return to zero within five seconds. FeNO measurements require a constant flow rate of three liters per minute for ten consecutive seconds.

By way of illustration, in one embodiment of the invention, the device can be constructed to make three respiratory measurements, e.g., (1) a spirometry test, which includes common tests such as PEF and FEV 1 wherein the user exhales forcefully into the device during a short time at rates ranging from 100 to 700 LPM, (2) a fractional exhaled nitric oxide test (FeNO) wherein the user exhales at a controlled rate of approximately 3 LPM over a period of approximately 10 seconds, and (3) a respiratory rate test. A large diaphragm shutter upstream of an optical-impeller based flow meter allows for the measurement of large, short duration flows of up to about 700 LPM when the leaf shutter is in the open position and air flow is substantially unrestricted through the device, e.g., the adjustable partition is in the open position, allowing for the free flow of the spirometry test to be exhausted out of the device. When the shutter is in its restricted position, air flow through the device is limited to no more than about 5 LPM, allowing for the NO test that requires the slow, steady exhalation of breath. In the restricted position, the air flows to the nitric oxide sensor, such as a solid-state nitric oxide sensor. In one embodiment, the restricted flow can be siphoned off, for example by a pump that siphons off the sample through the impeller shell hole, and delivered to the NO sensor. The pump can also be used to purge the device. The respiratory rate can be measured using an accelerometer that measures chest wall movements that correlate to breaths. In one embodiment, an accelerometer for measuring respirations (e.g., breaths per minute) can be coupled to the user's torso. Measurements from the accelerometer can be transmitted to the monitoring device of the present invention by wire, or wirelessly.

In addition to the above, in one embodiment the device is constructed to perform two other peripheral measurements: (1) pulse, and (2) pulse oximetry. These blood flow measurements can be made using optical sensors per standard methods.

With the above-described capabilities, the device can measure at least four markers that are of importance to asthma patients and doctors. Additional features and embodiments are described below.

As illustrated, a user generally exhales into the device through a mouthpiece. Any suitable mouthpiece may be employed in the practice of the invention described herein. However, it is advantageous to employ a mouthpiece that allows a user to inhale outside air through the mouthpiece, and exhale through the mouthpiece and into the device through a path separate from the path of inhaled air. It is further advantageous to filter the inhaled or exhaled air with one or more filtering media. One embodiment of such a mouthpiece is illustrated below.

Referring to FIGS. 19 to 22, a mouthpiece 401 is illustrated having a user side 403 and a device side 405. As a user inhales through the mouthpiece, fresh, outside air 409 enters the mouthpiece via one-way valve 407 and flows through a dedicated inhalation pathway 411 to the user. When the user exhales breath into the mouthpiece, the exhaled breath proceeds through a second dedicated pathway 413 through a second one-way valve 415 and then into the device.

As described above, the illustrated mouthpiece can contain one or more filters or filtering media. For example, referring more specifically to FIG. 22, a filtering media 417 for scrubbing $NO_x$ can be situated inside the mouthpiece adjacent to the one-way entry valve 407. In addition, an additional filter, such as a paper filter 419 can be incorporated into the device for filtering out microorganisms, such as bacteria or fungi. In addition, a desiccant, for example, can be included in the device for removing water vapor from exhaled breath that might otherwise enter the device and promote the growth of microorganisms or harm sensitive electronic components.

The filters or filtering media may be of any appropriate kind By way of illustration, filters and filtering media can be adopted for screening out gases of interest, including $NO_x$, $CO$, $CO_2$, $NH_3$, $O_2$, $H_2O$, etc. Examples of filtering media include activated alumina, Sofno-Fil, Sofno-Lime, silica, activated zeolite structures, and the like. Paper filters may be of any appropriate type for the intended function, for example, polypropylene, paper, cotton, or other fabric depending on the desired function.

The mouthpiece housing can be composed of any suitable materials. For example, the materials chosen should not interfere with the flow of the gases through the device or the filter materials. One such suitable material is polyethylene terephthalate (PET). The mouthpiece can be a single use, disposable component that can be sanitized prior to use or packaging, or easily sanitizable and reusable.

The described mouthpiece has numerous advantages. It can reduce the maintenance of monitors by moving the consumable filter media to a single use, disposable component. Or, in another embodiment, where the mouthpiece is reusable, filter media may be replaced or recharged as needed. This can reduce the need for monitor servicing, e.g., for the purpose of changing filter media or valves. This improves the cost efficiency of the monitors. Safety is increased because some breathing devices require the user to inhale through the device, potentially allowing bacteria or fungi from the device to enter the user. The described mouthpiece can also filter species that are detrimental to breath analyses.

In a particularly preferred device, the mouthpiece will operate with greater than fifty percent efficiency in the removal of specific species. For example, removal of moisture should reduce exhaled breath relative humidity to between 5 to 70%. Ingress and egress flow rates of between 25 to 300 sccm are desirable. Operating conditions should be ambient temperatures between 10 degrees Celsius to 45 degrees Celsius and relative humidity of between 5% to 99%.

In another embodiment of the present invention, pulmonary function, and other related tests, can be enhanced by incorporating a microcontroller. For example, a user can enter his or her data into the microcontroller, execute programs and receive the transmitted signals from integrated flow meter and NO sensor. The microcontroller can further include information storage means for storing entered parameters and received data.

In another embodiment, one or more gas sensors can be configured to measure clinically relevant-biomarkers, e.g., $H_2$, $CO$, or $O_2$ can be integrated with the present lung-function measuring device. Other sensing methods, e.g., electrochemical, acoustic, calorimetric, optical, or biological sensing methods can be incorporated for detecting gas molecules. For example, as described above, optical sensors (e.g., pulse oximetry) can be incorporated for measuring blood flow characteristics.

In another embodiment, the portable microcontroller can integrate with selected wired or wireless networks, e.g., Wi-Fi, Bluetooth, or USB to transmit and store data at remote locations. GPS can also be integrated to provide user location. For example, testing data can be automatically forwarded to a physician for monitoring and analysis.

In another embodiment, the device can obtain the user's location and local weather conditions, including air quality, and subsequently record and transmit this data. In a particularly preferred embodiment, fractionally exhaled nitric oxide concentration (FENO score) can be tracked and presented alongside tracking for other spirometry values such as FEV1, FEV6, PEV, FVC, TLC, and SVC, and alongside other environmental factors such as outside air temperature, weather conditions, wind speed, wind direction, barometer values, barometer trends, pollen count, air quality, ground level ozone, dew point, and humidity.

Figure 23:
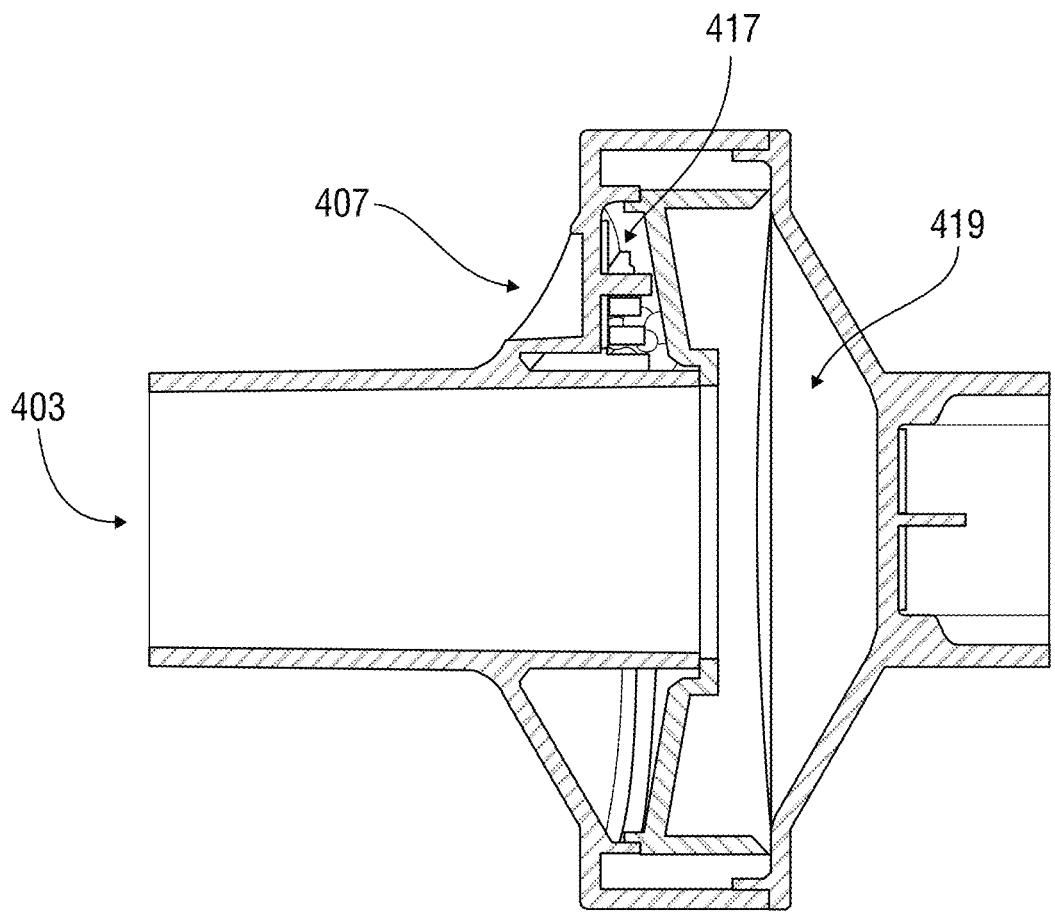
FIG. 23 is a side view of one embodiment of a multi-pathway mouthpiece.
Figure 24:
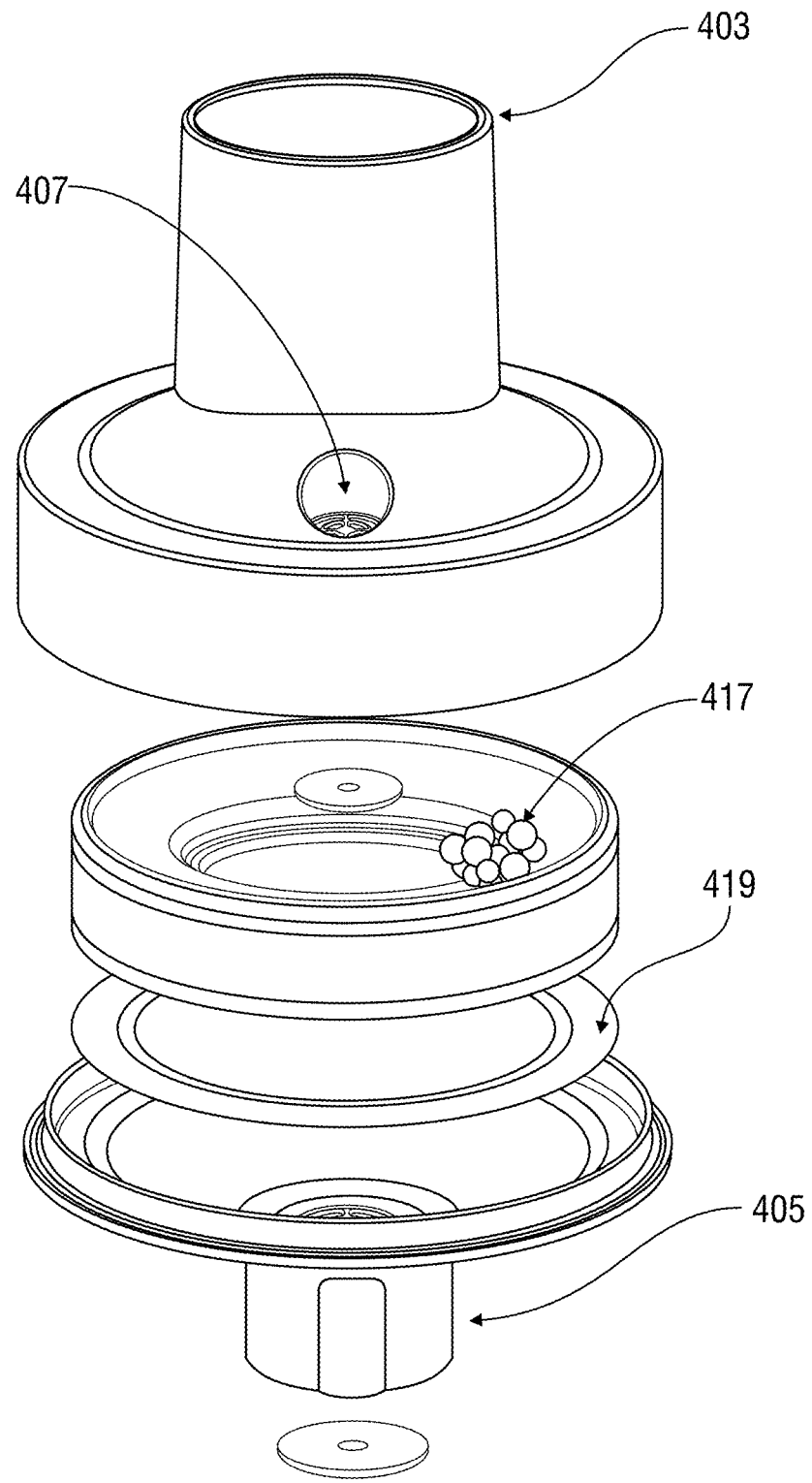
FIG. 24 is an exploded view of one embodiment of a multi-pathway mouthpiece.
Figure 25:
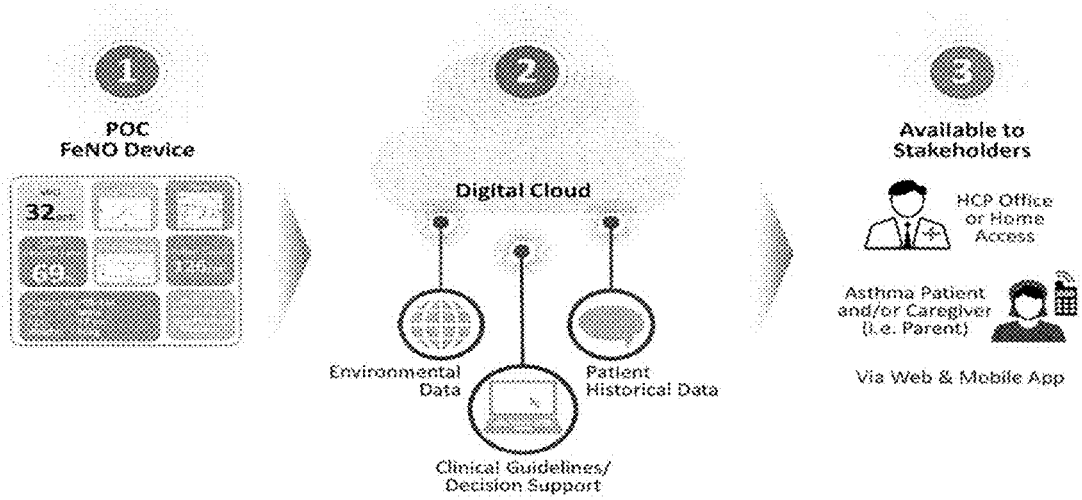
FIG. 25 is a schematic illustrating the connecting of an NO detection device to a network.

As a further illustration, the device 100 can be used with a data storage and information system to provide users and caregivers with asthma-related information. For example, referring to FIG. 23, the device 100 can be configured to connect via the internet to a cloud server. The device 100 can thus include a Wi-Fi, blue tooth, cellular, Ethernet or other connection to the internet. The cloud can include, for example, stored environmental data, such as air quality, air particle count, and other conditions, clinical guidelines, patient historical data, etc., which can then be relayed back to the user and or physician based upon the user's reading by way of the device 100, a web-based application, mobile device application, or local computer.

In some embodiments, the device can be configured to gather environmental data using a sensor built into the device. In other embodiments, the device's location can be determined by GPS or cellular triangulation, or Wi-Fi signal triangulation or other system sensor or a combination in whole or part of such systems and then querying a national and accepted data source for the above mentioned environmental parameters.

In other embodiments, the devices described herein can be used with a subscription service. For example, a physician can buy a subscription for so many uses of the device, then the physician will be granted access to the "ecosystem" database that can provide specific user results including but not limited to historical trends, local trends, regional trends, notifications may be such things as appointment reminders, or a notice of high pollen count within a nearby region that mayor may not correspond to particular NO reading, etc. The subscription service would also provide the user or physician the ability to record and or maintain a symptom diary that would be tracked along with exhaled nitric oxide measurements, and or any additional clinical or non-clinical data of interest to the user, physician, or other party.

As described above, there is an abundance of relevant medical and environmental parameters that bear on monitoring and evaluating an individual's respiratory functions. Relevant parameters also include an individual's activity and behavior parameters. The ability to collect, store, and analyze such parameters can be of tremendous benefit to patients, caregivers and healthcare professionals. With devices, such as those described herein, relevant parameters can be communicated to a secure computer network data system that collects, stores and analyzes such data. Moreover, once such data is collected and analyzed, it can be tracked and can be accessed via a customizable computer graphic interface. Consequently, the ability to simultaneously view such data in a customizable graphical user interface allows the plethora of available data to quicken the evaluation by healthcare professionals and individuals, such as patients.

Relevant medical parameters include, in addition to exhaled nitric oxide measurements, values obtained for other medical parameters of interest, such as nasal nitric oxide, exhaled CO and $CO_2$ levels, exhaled acetone, exhaled ketones, interleukin counts PEF, FEV1, FEV6, PEV, FVC, TLC, and SVC, blood eosinophil counts, blood oxidation levels, pulse oximetry, weight, height, BMI, and the like.

Environmental parameters include values such as ambient NO, air quality, airborne particle count temperature, dew point, wind speed, wind direction, pollen count, pollen blooms, smog, and the like. An individual's activity and behavior patterns include exercise and medication therapy adherence and the like.

As indicated, relevant medical and environmental data can be communicated, such as by uploading, to a computer network data system. Programs for analyzing, tracking and displaying the data can be computer based, cloud based or a combination. Access can be accomplished by any suitable computerized device that can display the information desired, such as desktops, laptops, tablets, mobile devices, and an appropriate respiratory monitor, such as those described herein, having a suitable microcontroller and graphical user interface display with access to the network that enable data communication between the device and the network such that data can be displayed on the accessing device, A computer implemented method for collection, storage, analysis, and facilitating access to the medical data and medically relevant data such as environmental parameters or patient behavioral data can be presented by a number of methods including but not limited to: graphs, plots, maps, pictures and tables for the purpose of providing environmental and behavioral context (potential correlation) to medical parameters of interest.

Networked diagnostic devices, such as those described herein, can send data to the networked system that includes date, time, location, user identification number, and clinical parameters such as exhaled nitric oxide concentration, and device specific information regarding device performance, etc. Networked diagnostic devices can also receive data from the networked system that includes active user identification numbers, and software update information, etc.

In a preferred embodiment, a network accessed graphical user interface is employed that will be displayed during access to the network that is capable of displaying queried data in the form of graphs, charts, maps, pictures, and tables in a specific format based on the user's preference and access level. Further the user interface will be capable of determining and maintaining security based on the user's level of access, but always transmitting data in such a manner that it uses appropriate security measures, such as encoding, encryption, pass-key access, etc.

The network accessed graphical user interface may be primarily used to display a single patient profile that would include that specific patient's specified medical parameter historical data shown on a trend chart. Such trend charts can display a single, or a plurality of medical parameters using the equivalent time based scale and such that the axis are consistent or matching orientations of goodness. For example FEV 1 can be displayed as a percentage of 100 where 100% is good. FeNO can be shown on scale of 5-300 where low numbers are good. The FeNO score can be oriented such that the lowest score (5 ppb) is oriented at the top (up). Additional parameters selected by the user for display can be presented in similar fashion In addition, at the preference of a user, medical parameter trends can be simultaneously displayed with environmental data trended by the location preference chosen by the user. For example, a patient and their doctor's office are often not co-located, thus when a health care professional (HCP) is reviewing a patient's profile, the HCP may elect to view FeNO scores simultaneously with the air quality historical data for the HCP's office, or it maybe displayed with the air quality historical data from the patient's home address, city, zip code, or other means of geo-locating. Moreover, the graphical user interface can display historical data trends that may include special notes regarding specific data points. For example, in the context of FeNO measurements and geo-location, it can be noted where a particular patient may have traveled in between or during a particular evaluation. As such, an environment not typically listed (HCP office, home, work, etc.) can be noted and taken into account.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with anyone or more of the features described herein. The breadth of the present invention is not to be limited by the subject specification, but rather only by the plain meaning of the claim terms employed.

This disclosure is sufficient to enable one of ordinary skill in the art to practice the invention, and provides the best mode of practicing the invention presently contemplated by the inventor. While a full and complete disclosure is made of specific embodiments of this invention, the invention is not limited by the exact construction, dimensional relationships, and operation shown and described. Various modifications, alternative constructions, design options, changes and equivalents will be readily apparent to those skilled in the art and may be employed, as suitable, without departing from the spirit and scope of the invention. Such changes might involve alternative materials, components, structural arrangements, sizes, shapes, forms, functions, operational features and the like.

What is claimed is:
1. An apparatus, comprising:
   a. a housing;
   b. a gas inlet section positioned in the housing, comprising:
      i. a flow detection component positioned within the gas inlet section;
      ii. an adjustable partition positioned downstream from the flow detection component;
      iii. a humidity equilibrator positioned downstream from the adjustable partition;
      iv. an adjustable flow-restriction component configured to partition the gas inlet section upstream from the humidity equilibrator; and
      v. an adjustable inlet for ambient air positioned downstream from the adjustable partition and upstream from the humidity equilibrator; and
   c. a measuring assembly located adjacent to and in fluid communication with the gas inlet section; wherein the measuring assembly is configured to determine the total nitric oxide (NO) concentration from an incoming gas sample.
2. A method of determining total nitrogen oxides ($NO_x$) concentration from a breath sample, comprising:
   a. collecting a breath sample from a user using a mouthpiece;
   b. flowing the breath sample from the mouthpiece to an inlet portal of an analyzer;
   c. flowing the breath sample from the inlet portal of the analyzer to an adjustable flow restrictor positioned within the analyzer;
   d. equilibrating the moisture content in the breath sample flowing from the inlet portal and through the analyzer to ambient conditions;
   e. admitting ambient air through the analyzer through an adjustable inlet positioned upstream from a humidity equilibrator;
   f. forming an equilibrium mixture of nitric oxide (NO) and nitrogen dioxide ($NO_2$) from $NO_x$ in the breath sample using a platinum-zeolite reactor element;
   g. measuring $NO_x$ concentration in the breath sample using a sensor element located downstream from the reactor element;
   h. determining total NO concentration in the breath sample based on the measured $NO_x$ concentration and equilibrium mixture; and
   i. releasing the breath sample through an exhaust portal.

* * * * *